US008933034B2

(12) United States Patent
Ford

(10) Patent No.: US 8,933,034 B2
(45) Date of Patent: *Jan. 13, 2015

(54) CHIMERIC NEUREGULINS AND METHOD OF MAKING AND USE THEREOF

(71) Applicant: Byron D. Ford, Duluth, GA (US)

(72) Inventor: Byron D. Ford, Duluth, GA (US)

(73) Assignee: Brain-Gen Biotech, Duluth, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/865,812

(22) Filed: Apr. 18, 2013

(65) Prior Publication Data

US 2014/0086897 A1  Mar. 27, 2014
US 2014/0227247 A2  Aug. 14, 2014

Related U.S. Application Data

(63) Continuation of application No. 13/627,555, filed on Sep. 26, 2012, now Pat. No. 8,748,131.

(51) Int. Cl.
| | |
|---|---|
| C07K 14/475 | (2006.01) |
| C07K 14/48 | (2006.01) |
| C07K 16/18 | (2006.01) |
| A61K 38/18 | (2006.01) |
| A61K 45/06 | (2006.01) |
| A61K 38/49 | (2006.01) |
| A61K 38/48 | (2006.01) |

(52) U.S. Cl.
CPC ............ *A61K 38/1883* (2013.01); *A61K 45/06* (2013.01); *A61K 38/49* (2013.01); *A61K 38/482* (2013.01)
USPC ....... 514/17.7; 435/69.4; 435/69.6; 435/7.21; 435/326; 435/69.7; 530/300; 530/399; 514/8.3

(58) Field of Classification Search
None
See application file for complete search history.

(56) References Cited

U.S. PATENT DOCUMENTS

| | | | |
|---|---|---|---|
| 4,522,811 A | 6/1985 | Eppstein et al. | |
| 7,776,817 B2 * | 8/2010 | Ford | 514/8.4 |

OTHER PUBLICATIONS

Ieguchi et al., Direct Binding of the EGF-like Domain of Neuregulin-1 to Integrins (Aplha v Beta 3 and Aplha 6 Beta4) Is Involved in Neuregulin-1/ErbB Signaling. J. Biol. Chem. 2010, 285:31388-31398.*
Higashiyama et al., A Novel Brain-Derived Member of the Epidermal Growth Factor Family That Interacts with ErbB3 and ErbB4. J. Biochem. 122, 675-680 (1997).*
Fischbach et al., "ARIA: A Neuromuscular Junction Neuregulin," Annual Review of Neuroscience, 1997, pp. 429-458, vol. 20.
Buonanno et al., "Neuregulin and ErbB receptor signaling pathways in the nervous system," Current Opinion in Neurobiology, 2001, pp. 287-296, vol. 11.

(Continued)

*Primary Examiner* — Gregory S Emch
*Assistant Examiner* — Aurora M Fontainhas
(74) *Attorney, Agent, or Firm* — Ping Wang; Andrews Kurth LLP

(57) ABSTRACT

Composition containing a chimeric neuregulin polypeptides and method of making such polypeptides are disclosed. The chimeric neuregulin comprises a first moiety of at least 10 amino acids, wherein the first moiety is derived from a first polypeptide; and a second moiety of at least 5 amino acids, wherein the second moiety is derived from a second polypeptide; wherein the first polypeptide is a neuregulin and the chimeric neuregulin exhibits an enhanced binding affinity to integrin, Erb 3, or Erb 4 comparing to that of the first neuregulin.

14 Claims, 11 Drawing Sheets

(56) References Cited

OTHER PUBLICATIONS

Burden et al., "Neuregulins and Their Receptors: A Versatile Signaling Module in Organogenesis and Oncogenesis," Neuron, 1997, pp. 847-855, vol. 18.

Holmes et al., "Identification of Heregulin, a Specific Activator of p185erbB2," Science, May 22, 1992, pp. 1205-1210, vol. 256.

Fu et al., "Cdk5 is involved in neuregulin-induced AChR expression at the neuromuscular junction," Nature Neuroscience, Apr. 2001, pp. 374-381, vol. 4—No. 4.

Chang et al., "Ligands for ErbB-family receptors encoded by a neuregulin-like gene," Nature, May 29, 1997, pp. 509-512, vol. 387.

Carraway et al., "Neuregulin-2, a new ligand of ErbB3/ErbB4-receptor tyrosine kinases," Nature, 1997, pp. 512-516, vol. 387.

Zhang et al., "Neuregulin-3 (NRG3): A novel neural tissue-enriched protein that binds and activates ErbB4," Proceedings of the National Academy of Science U.S.A., Sep. 1997, pp. 9562-9567, vol. 94.

Chen et al., "Fine Mapping on Chromosome 10q22-q23 Implicates Neuregulin 3 in Schizophrenia," The American Journal of Human Genetics, Jan. 9, 2009, pp. 21-34, vol. 84.

Harari et al., "Neuregulin-4: a novel growth factor that acts through the ErbB-4 receptor tyrosine kinase," Oncogene, 1999, pp. 2681-2689, vol. 18.

Memon et al., "Expression of HER3, HER4 and their ligand heregulin-4 is associated with better survival in bladder cancer patients," British Jounal of Cancer, 2004, pp. 2034-2041, vol. 91.

Van Heeke et al., "Expression of Human Asparagine Synthetase in *Escherichia coli*," The Journal of Biological Chemistry, Apr. 5, 1989, pp. 5503-5509, vol. 264—No. 10.

Belayev et al., "Bilateral ischemic tolerance of rat hippocampus induced by prior unilateral transient focal ischemia: relationship to c-fos mRNA expression," NeuroReport, Dec. 20, 1996, pp. 55-59, vol. 8—No. 1.

Belayev et al., "Post-ischemic administration of HU-211, a novel non-competitive NMDA antagonist, protects against blood-brain barrier disruption in photochemical cortical infarction in rats: a quantitative study," Brain Research, 1995, pp. 266-270, vol. 702.

Menzies et al., "Human Placental Gonadotrophin-Releasing Hormone (GnRH) Binding Sites: II. Comparison of Binding and Inactivation of 125I-Labelled GnRH agonist to Subcellular Fractions following Density Gradient Centrifugation," Placenta, 1992, pp. 583-595, vol. 13.

File history of U.S. Appl. No. 13/627,555, filed Sep. 26, 2012.

U.S. Appl. No. 13/627,555, filed Sep. 26, 2012.

PCT/US2012/57272, Sep. 26, 2012.

\* cited by examiner

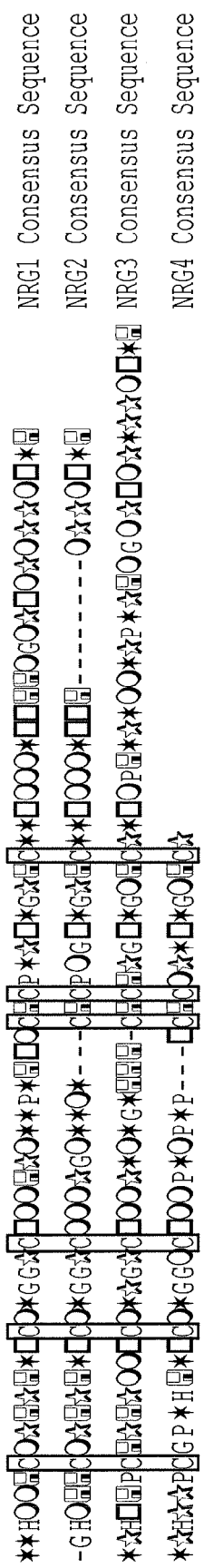

FIG. 2

```
--HLVKCAEKEKTFCVNGGECFMVKDLSNPSRYLCKCPNEFTGDRCQNYVMASFY------    NRG1
--HLVKCAEKEKTFCVNGGECFMVKDLSNPSRYLCKCQPGFTGARCTENVMASFY------    NRG1/ HRGβ hybrid, SEQ ID NO:20)
-GHARKCNETAKSYCVNGGECYYIEGINQLS---CKCPNGFFGQRCLEKLPLRLYKAEELYQK  (NRG1/ HRGα/β hybrid, SEQ ID NO:21)
-GHARKCNETAKSYCVNGGECYYIEGINQLS---CKCQPNGFFGQRCQNYVMASFY------   (NRG2.2/NRG1 hybrid, SEQ ID NO:22)
--HARKCNETAKSYCVNGGECFMVKDLSNPSRYLCKCPNEFTGDRCQNYVMASFY------    (NRG2/GGF2 hybrid, SEQ ID NO:23)
-GHARKCAEKEKTFCVNGGECFMVKDLSNPSRYLCKCPNEFTGDRCQNYVMASFY------    (NRG2/NRG2 hybrid, SEQ ID NO:24)
--HLVKCAEKEKTFCLNGGLCYVIPTIPSP----FCRCVENYTGARCE--------------  (GGF2/NRG2/GGF2 hybrid, SEQ ID NO:25)
--HARKCAEKEKTFCLNGGLCYVIPTIPSP----FCRCVENYTGARCE--------------  (NRG1/NRG4 hybrid, SEQ ID NO:26)
--HARKCNETAKSYCVNGGECYYIEGINQLS---CKCQPNGFFGQRCQNYVMASFY------  (NRG1/NRG4 hybrid, (SEQ ID NO:27)
TDHEEPCGPSHKSFCLNGGLCYVIPTIPSP----FCKCPNGFFGQRCQNYVMASFY------  (NRG1/NRG2/NRG4 hybrid, SEQ ID NO:28)
                                                                 (NRG4/NRG1 hybrid, SEQ ID NO:29)
```

FIG. 3

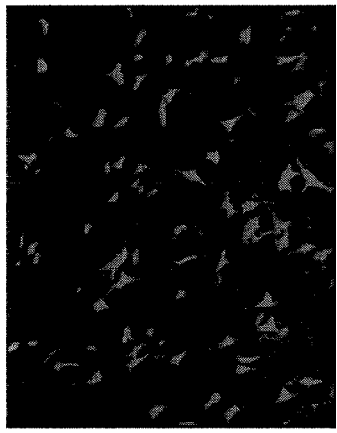 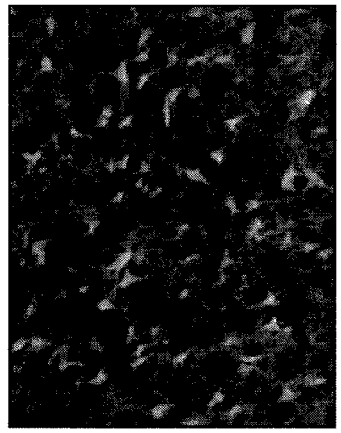 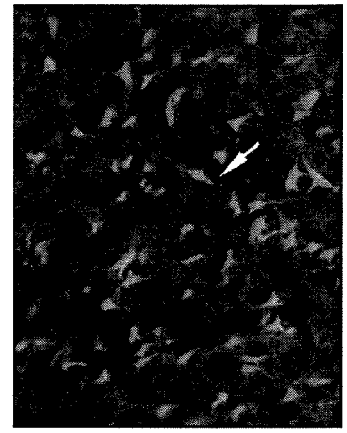
*FIG. 4A*  *FIG. 4B*  *FIG. 4C*
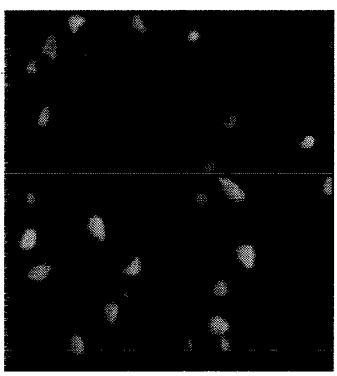 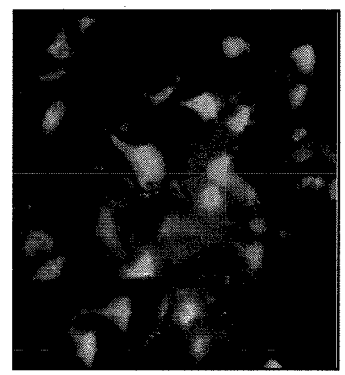 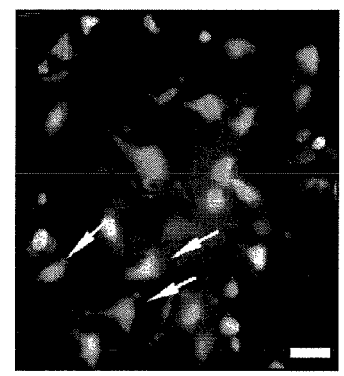
*FIG. 4D*  *FIG. 4E*  *FIG. 4F*

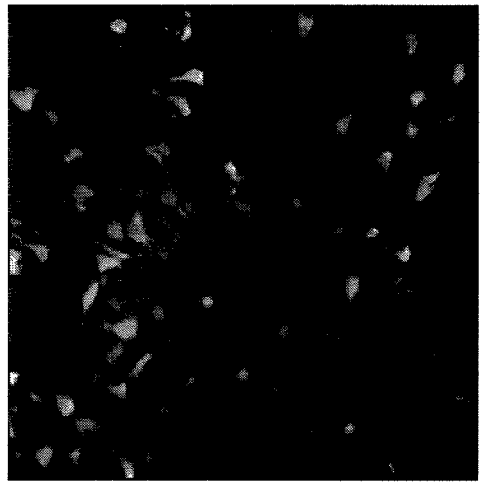
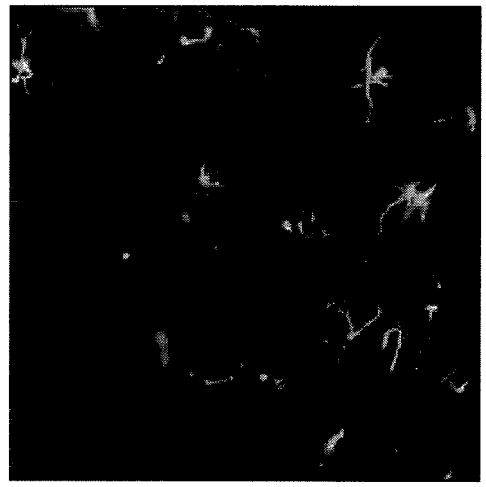
FIG. 5A  FIG. 5B
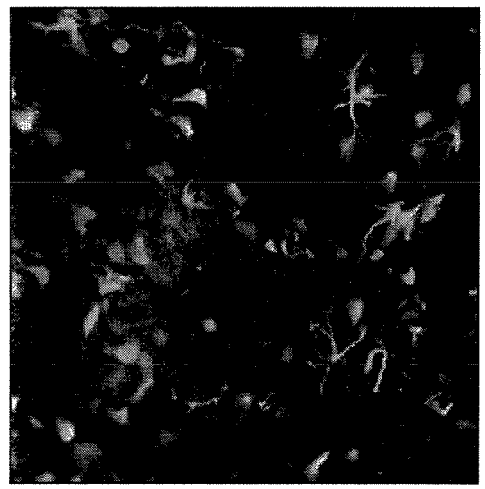
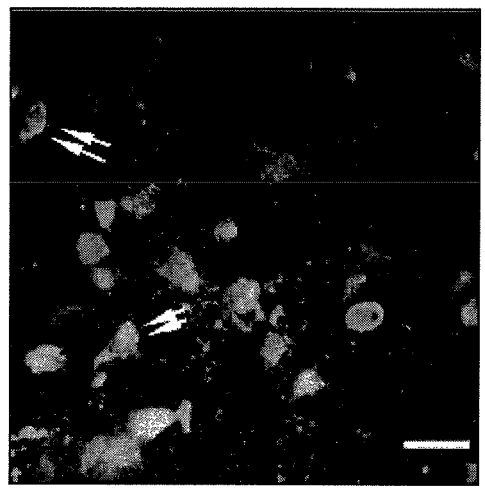
FIG. 5C  FIG. 5D

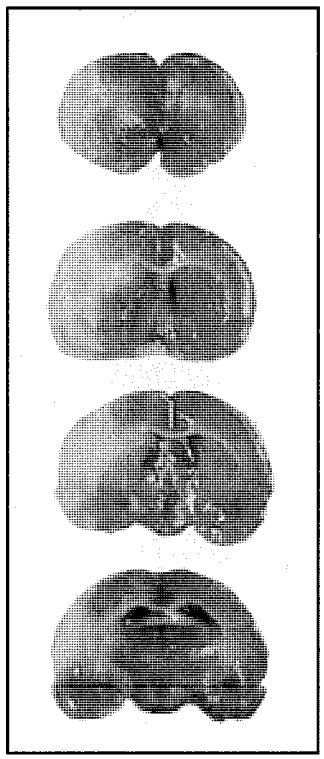 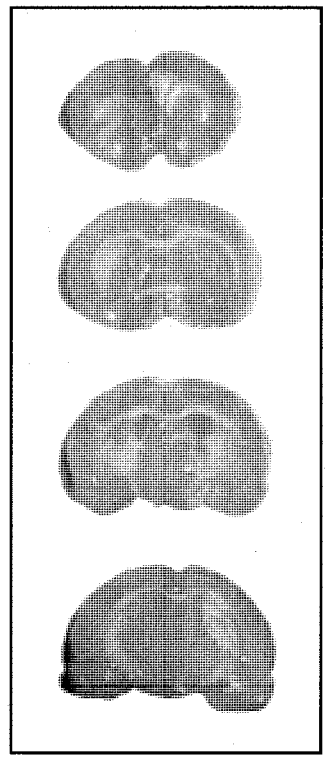 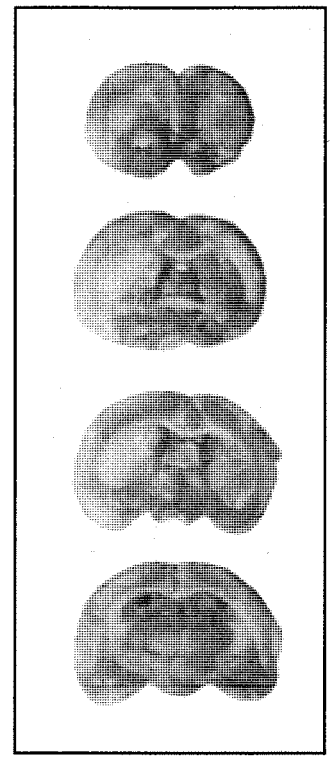
*FIG. 6A*  *FIG. 6B*  *FIG. 6C*
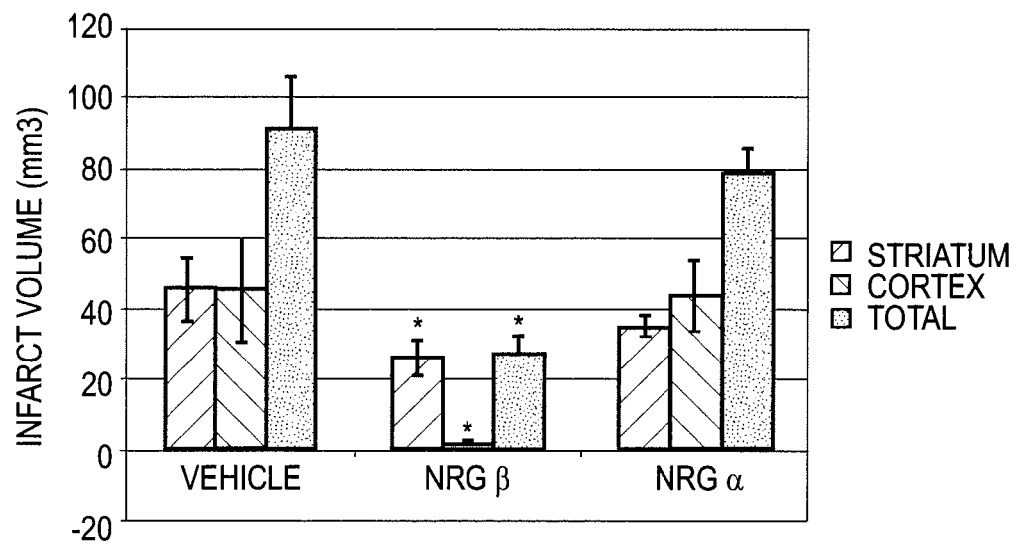
*FIG. 6D*

SEQUENCE LISTING

```
<160> NUMBER OF SEQ ID NOS: 29

<210> SEQ ID NO 1
<211> LENGTH: 70
<212> TYPE: PRT
<213> ORGANISM: Homo sapiens

<400> SEQUENCE: 1

Thr Ser His Leu Val Lys Cys Ala Glu Lys Glu Lys Thr Phe Cys Val
1               5                   10                  15

Asn Gly Gly Glu Cys Phe Met Val Lys Asp Leu Ser Asn Pro Ser Arg
            20                  25                  30

Tyr Leu Cys Lys Cys Pro Asn Glu Phe Thr Gly Asp Arg Cys Gln Asn
        35                  40                  45

Tyr Val Met Ala Ser Phe Tyr Lys His Leu Gly Ile Glu Phe Met Glu
    50                  55                  60

Ala Glu Glu Leu Tyr Gln
65                  70

<210> SEQ ID NO 2
<211> LENGTH: 71
<212> TYPE: PRT
<213> ORGANISM: Homo sapiens

<400> SEQUENCE: 2

Thr Ser His Leu Val Lys Cys Ala Glu Lys Glu Lys Ala Phe Cys Val
1               5                   10                  15

Asn Gly Gly Glu Cys Phe Met Val Lys Asp Leu Ser Asn Pro Ser Arg
            20                  25                  30
```

Tyr Leu Cys Lys Cys Pro Asn Glu Phe Thr Gly Asp Arg Cys Gln Asn
             35                  40                  45

Tyr Val Met Ala Ser Phe Tyr Lys His Leu Gly Ile Glu Phe Met Glu
     50                  55                  60

Ala Glu Glu Leu Tyr Gln Lys
 65                  70

<210> SEQ ID NO 3
<211> LENGTH: 55
<212> TYPE: PRT
<213> ORGANISM: Homo sapiens

<400> SEQUENCE: 3

Thr Ser His Leu Val Lys Cys Ala Glu Lys Glu Lys Thr Phe Cys Val
 1               5                  10                  15

Asn Gly Gly Glu Cys Phe Met Val Lys Asp Leu Ser Asn Pro Ser Arg
             20                  25                  30

Tyr Leu Cys Lys Cys Pro Asn Glu Phe Thr Gly Asp Arg Cys Gln Asn
             35                  40                  45

Tyr Val Met Ala Ser Phe Tyr
     50                  55

<210> SEQ ID NO 4
<211> LENGTH: 61
<212> TYPE: PRT
<213> ORGANISM: Homo sapiens

<400> SEQUENCE: 4

His Leu Val Lys Cys Ala Glu Lys Glu Lys Thr Phe Cys Val Asn Gly
 1               5                  10                  15

Gly Glu Cys Phe Met Val Lys Asp Leu Ser Asn Pro Ser Arg Tyr Leu
             20                  25                  30

Cys Lys Cys Pro Asn Glu Phe Thr Gly Asp Arg Cys Gln Asn Tyr Val
             35                  40                  45

Met Ala Ser Phe Tyr Lys Ala Glu Glu Leu Tyr Gln Lys
     50                  55                  60

<210> SEQ ID NO 5
<211> LENGTH: 34
<212> TYPE: PRT
<213> ORGANISM: Homo sapiens

<400> SEQUENCE: 5

His Leu Val Lys Cys Ala Glu Lys Glu Lys Thr Phe Cys Val Asn Gly
 1               5                  10                  15

Gly Glu Cys Phe Met Val Lys Asp Leu Ser Asn Pro Ser Arg Tyr Leu
             20                  25                  30

Cys Lys

<210> SEQ ID NO 6
<211> LENGTH: 36
<212> TYPE: PRT
<213> ORGANISM: Homo sapiens

<400> SEQUENCE: 6

Cys Val Asn Gly Gly Glu Cys Phe Met Val Lys Asp Leu Ser Asn Pro
 1               5                  10                  15

Ser Arg Tyr Leu Cys Lys Cys Gln Pro Gly Phe Thr Gly Ala Arg Cys
             20                  25                  30

```
Thr Glu Asn Val
        35

<210> SEQ ID NO 7
<211> LENGTH: 66
<212> TYPE: PRT
<213> ORGANISM: Homo sapiens

<400> SEQUENCE: 7

Thr Ser His Leu Val Lys Cys Ala Glu Lys Glu Lys Thr Phe Cys Val
1               5                   10                  15

Asn Gly Gly Glu Cys Phe Met Val Lys Asp Leu Ser Asn Pro Ser Arg
            20                  25                  30

Tyr Leu Cys Lys Cys Gln Pro Gly Phe Thr Gly Ala Arg Cys Thr Glu
        35                  40                  45

Asn Val Pro Met Lys Val Gln Asn Gln Glu Lys Ala Glu Glu Leu Tyr
    50                  55                  60

Gln Lys
65

<210> SEQ ID NO 8
<211> LENGTH: 65
<212> TYPE: PRT
<213> ORGANISM: Homo sapiens

<400> SEQUENCE: 8

Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30

Leu Cys Lys Cys Gln Pro Gly Phe Thr Gly Ala Arg Cys Thr Glu Asn
        35                  40                  45

Val Pro Met Lys Val Gln Asn Gln Glu Lys Ala Glu Glu Leu Tyr Gln
    50                  55                  60

Lys
65

<210> SEQ ID NO 9
<211> LENGTH: 64
<212> TYPE: PRT
<213> ORGANISM: Homo sapiens

<400> SEQUENCE: 9

His Leu Val Lys Cys Ala Glu Lys Glu Lys Thr Phe Cys Val Asn Gly
1               5                   10                  15

Gly Glu Cys Phe Met Val Lys Asp Leu Ser Asn Pro Ser Arg Tyr Leu
            20                  25                  30

Cys Lys Cys Gln Pro Gly Phe Thr Gly Ala Arg Cys Thr Glu Asn Val
        35                  40                  45

Pro Met Lys Val Gln Asn Gln Glu Lys Ala Glu Glu Leu Tyr Gln Lys
    50                  55                  60

<210> SEQ ID NO 10
<211> LENGTH: 48
<212> TYPE: PRT
<213> ORGANISM: Homo sapiens

<400> SEQUENCE: 10

His Leu Val Lys Cys Ala Glu Lys Glu Lys Thr Phe Cys Val Asn Gly
```

```
                1               5                  10                  15
Gly Glu Cys Phe Met Val Lys Asp Leu Ser Asn Pro Ser Arg Tyr Leu
                20                  25                  30

Cys Lys Cys Gln Pro Gly Phe Thr Gly Ala Arg Cys Thr Glu Asn Val
        35                  40                  45
```

<210> SEQ ID NO 11
<211> LENGTH: 68
<212> TYPE: PRT
<213> ORGANISM: Homo sapiens

<400> SEQUENCE: 11

```
Ser Gly His Ala Arg Lys Cys Asn Glu Thr Ala Lys Ser Tyr Cys Val
1               5                  10                  15

Asn Gly Gly Val Cys Tyr Tyr Ile Glu Gly Ile Asn Gln Leu Ser Cys
                20                  25                  30

Lys Cys Pro Val Gly Tyr Thr Gly Asp Arg Cys Gln Gln Phe Ala Met
        35                  40                  45

Val Asn Phe Ser Lys His Leu Gly Phe Glu Leu Lys Glu Ala Glu Glu
        50                  55                  60

Leu Tyr Gln Lys
65
```

<210> SEQ ID NO 12
<211> LENGTH: 52
<212> TYPE: PRT
<213> ORGANISM: Homo sapiens

<400> SEQUENCE: 12

```
Ser Gly His Ala Arg Lys Cys Asn Glu Thr Ala Lys Ser Tyr Cys Val
1               5                  10                  15

Asn Gly Gly Val Cys Tyr Tyr Ile Glu Gly Ile Asn Gln Leu Ser Cys
                20                  25                  30

Lys Cys Pro Asn Gly Phe Phe Gly Gln Arg Cys Leu Glu Lys Leu Pro
        35                  40                  45

Leu Arg Leu Tyr
    50
```

<210> SEQ ID NO 13
<211> LENGTH: 74
<212> TYPE: PRT
<213> ORGANISM: Homo sapiens

<400> SEQUENCE: 13

```
Ser Gly His Ala Arg Lys Cys Asn Glu Thr Ala Lys Ser Tyr Cys Val
1               5                  10                  15

Asn Gly Gly Val Cys Tyr Tyr Ile Glu Gly Ile Asn Gln Leu Ser Cys
                20                  25                  30

Lys Cys Pro Asn Gly Phe Phe Gly Gln Arg Cys Leu Glu Lys Leu Pro
        35                  40                  45

Leu Arg Leu Tyr Met Pro Asp Pro Lys Gln Lys His Leu Gly Phe Glu
        50                  55                  60

Leu Lys Glu Ala Glu Glu Leu Tyr Gln Lys
65                  70
```

<210> SEQ ID NO 14
<211> LENGTH: 59
<212> TYPE: PRT
<213> ORGANISM: Homo sapiens

<400> SEQUENCE: 14

Gly His Ala Arg Lys Cys Asn Glu Thr Ala Lys Ser Tyr Cys Val Asn
1               5                   10                  15

Gly Gly Val Cys Tyr Tyr Ile Glu Gly Ile Asn Gln Leu Ser Cys Lys
            20                  25                  30

Cys Pro Val Gly Tyr Thr Gly Asp Arg Cys Gln Gln Phe Ala Met Val
        35                  40                  45

Asn Phe Ser Lys Ala Glu Glu Leu Tyr Gln Lys
    50                  55

<210> SEQ ID NO 15
<211> LENGTH: 56
<212> TYPE: PRT
<213> ORGANISM: Homo sapiens

<400> SEQUENCE: 15

Gly Glu Cys Phe Met Val Lys Asp Leu Ser Asn Pro Ser Arg Tyr Leu
1               5                   10                  15

Cys Lys Cys Gln Pro Gly Phe Thr Gly Ala Arg Cys Thr Glu Asn Val
            20                  25                  30

Pro Met Lys Val Gln Asn Gln Glu Lys His Leu Gly Ile Glu Phe Ile
        35                  40                  45

Glu Ala Glu Glu Leu Tyr Gln Lys
    50                  55

<210> SEQ ID NO 16
<211> LENGTH: 75
<212> TYPE: PRT
<213> ORGANISM: Homo sapiens

<400> SEQUENCE: 16

Ser Glu His Phe Lys Pro Cys Arg Asp Lys Asp Leu Ala Tyr Cys Leu
1               5                   10                  15

Asn Asp Gly Glu Cys Phe Val Ile Glu Thr Leu Thr Gly Ser His Lys
            20                  25                  30

His Cys Arg Cys Lys Glu Gly Tyr Gln Gly Val Arg Cys Asp Gln Phe
        35                  40                  45

Leu Pro Lys Thr Asp Ser Ile Leu Ser Asp Pro Asn His Leu Gly Ile
    50                  55                  60

Glu Phe Met Glu Ser Glu Glu Val Tyr Gln Arg
65                  70                  75

<210> SEQ ID NO 17
<211> LENGTH: 76
<212> TYPE: PRT
<213> ORGANISM: Homo sapiens

<400> SEQUENCE: 17

Ser Glu His Phe Lys Pro Cys Arg Asp Lys Asp Leu Ala Tyr Cys Leu
1               5                   10                  15

Asn Asp Gly Glu Cys Phe Val Ile Glu Thr Leu Thr Gly Ser His Lys
            20                  25                  30

His Cys Arg Cys Lys Glu Gly Tyr Gln Gly Val Arg Cys Asp Gln Phe
        35                  40                  45

Leu Pro Lys Thr Asp Ser Ile Leu Ser Asp Pro Thr Asp His Leu Gly
    50                  55                  60

Ile Glu Phe Met Glu Ser Glu Glu Val Tyr Gln Arg 65            70            75

<210> SEQ ID NO 18
<211> LENGTH: 49
<212> TYPE: PRT
<213> ORGANISM: Homo sapiens

<400> SEQUENCE: 18

Ser Glu His Phe Lys Pro Cys Arg Asp Lys Asp Leu Ala Tyr Cys Leu
1               5                   10                  15

Asn Asp Gly Glu Cys Phe Val Ile Glu Thr Leu Thr Gly Ser His Lys
            20                  25                  30

His Cys Arg Cys Lys Glu Gly Tyr Gln Gly Val Arg Cys Asp Gln Phe
        35                  40                  45

Leu

<210> SEQ ID NO 19
<211> LENGTH: 44
<212> TYPE: PRT
<213> ORGANISM: Homo sapiens

<400> SEQUENCE: 19

Thr Asp His Glu Glu Pro Cys Gly Pro Ser His Lys Ser Phe Cys Leu
1               5                   10                  15

Asn Gly Gly Leu Cys Tyr Val Ile Pro Thr Ile Pro Ser Pro Phe Cys
            20                  25                  30

Arg Cys Val Glu Asn Tyr Thr Gly Ala Arg Cys Glu
        35                  40

<210> SEQ ID NO 20
<211> LENGTH: 53
<212> TYPE: PRT
<213> ORGANISM: artificial
<220> FEATURE:
<223> OTHER INFORMATION: hybrid polypeptide

<400> SEQUENCE: 20

His Leu Val Lys Cys Ala Glu Lys Glu Lys Thr Phe Cys Val Asn Gly
1               5                   10                  15

Gly Glu Cys Phe Met Val Lys Asp Leu Ser Asn Pro Ser Arg Tyr Leu
            20                  25                  30

Cys Lys Cys Pro Asn Glu Phe Thr Gly Asp Arg Cys Gln Asn Tyr Val
        35                  40                  45

Met Ala Ser Phe Tyr
    50

<210> SEQ ID NO 21
<211> LENGTH: 53
<212> TYPE: PRT
<213> ORGANISM: artificial
<220> FEATURE:
<223> OTHER INFORMATION: hybrid polypeptide

<400> SEQUENCE: 21

His Leu Val Lys Cys Ala Glu Lys Glu Lys Thr Phe Cys Val Asn Gly
1               5                   10                  15

Gly Glu Cys Phe Met Val Lys Asp Leu Ser Asn Pro Ser Arg Tyr Leu
            20                  25                  30

Cys Lys Cys Gln Pro Gly Phe Thr Gly Ala Arg Cys Thr Glu Asn Val
        35                  40                  45

Met Ala Ser Phe Tyr
        50

<210> SEQ ID NO 22
<211> LENGTH: 59
<212> TYPE: PRT
<213> ORGANISM: artificial
<220> FEATURE:
<223> OTHER INFORMATION: hybrid polypeptide

<400> SEQUENCE: 22

Gly His Ala Arg Lys Cys Asn Glu Thr Ala Lys Ser Tyr Cys Val Asn
1               5                   10                  15

Gly Gly Val Cys Tyr Tyr Ile Glu Gly Ile Asn Gln Leu Ser Cys Lys
            20                  25                  30

Cys Pro Asn Gly Phe Phe Gly Gln Arg Cys Leu Glu Lys Leu Pro Leu
        35                  40                  45

Arg Leu Tyr Lys Ala Glu Glu Leu Tyr Gln Lys
    50                  55

<210> SEQ ID NO 23
<211> LENGTH: 51
<212> TYPE: PRT
<213> ORGANISM: artificial
<220> FEATURE:
<223> OTHER INFORMATION: hybrid polypeptide

<400> SEQUENCE: 23

Gly His Ala Arg Lys Cys Asn Glu Thr Ala Lys Ser Tyr Cys Val Asn
1               5                   10                  15

Gly Gly Val Cys Tyr Tyr Ile Glu Gly Ile Asn Gln Leu Ser Cys Lys
            20                  25                  30

Cys Pro Asn Gly Phe Phe Gly Gln Arg Cys Gln Asn Tyr Val Met Ala
        35                  40                  45

Ser Phe Tyr
    50

<210> SEQ ID NO 24
<211> LENGTH: 53
<212> TYPE: PRT
<213> ORGANISM: artificial
<220> FEATURE:
<223> OTHER INFORMATION: hybrid polypeptide

<400> SEQUENCE: 24

His Ala Arg Lys Cys Ala Glu Lys Glu Lys Thr Phe Cys Val Asn Gly
1               5                   10                  15

Gly Glu Cys Phe Met Val Lys Asp Leu Ser Asn Pro Ser Arg Tyr Leu
            20                  25                  30

Cys Lys Cys Pro Asn Glu Phe Thr Gly Asp Arg Cys Gln Asn Tyr Val
        35                  40                  45

Met Ala Ser Phe Tyr
    50

<210> SEQ ID NO 25
<211> LENGTH: 51
<212> TYPE: PRT
<213> ORGANISM: artificial
<220> FEATURE:
<223> OTHER INFORMATION: hybrid polypeptide

<400> SEQUENCE: 25

```
Gly His Ala Arg Lys Cys Ala Glu Lys Glu Lys Thr Phe Cys Val Asn
1               5                   10                  15

Gly Gly Val Cys Tyr Tyr Ile Glu Gly Ile Asn Gln Leu Ser Cys Lys
            20                  25                  30

Cys Pro Asn Gly Phe Phe Gly Gln Arg Cys Gln Asn Tyr Val Met Ala
        35                  40                  45

Ser Phe Tyr
    50

<210> SEQ ID NO 26
<211> LENGTH: 42
<212> TYPE: PRT
<213> ORGANISM: artificial
<220> FEATURE:
<223> OTHER INFORMATION: hybrid polypeptide

<400> SEQUENCE: 26

His Leu Val Lys Cys Ala Glu Lys Glu Lys Thr Phe Cys Leu Asn Gly
1               5                   10                  15

Gly Leu Cys Tyr Val Ile Pro Thr Ile Pro Ser Pro Phe Cys Arg Cys
            20                  25                  30

Val Glu Asn Tyr Thr Gly Ala Arg Cys Glu
        35                  40

<210> SEQ ID NO 27
<211> LENGTH: 42
<212> TYPE: PRT
<213> ORGANISM: artificial
<220> FEATURE:
<223> OTHER INFORMATION: htbrid polypeptide

<400> SEQUENCE: 27

His Ala Arg Lys Cys Ala Glu Lys Glu Lys Thr Phe Cys Leu Asn Gly
1               5                   10                  15

Gly Leu Cys Tyr Val Ile Pro Thr Ile Pro Ser Pro Phe Cys Arg Cys
            20                  25                  30

Val Glu Asn Tyr Thr Gly Ala Arg Cys Glu
        35                  40

<210> SEQ ID NO 28
<211> LENGTH: 50
<212> TYPE: PRT
<213> ORGANISM: artificial
<220> FEATURE:
<223> OTHER INFORMATION: hybrid polypeptide

<400> SEQUENCE: 28

His Ala Arg Lys Cys Asn Glu Thr Ala Lys Ser Tyr Cys Val Asn Gly
1               5                   10                  15

Gly Val Cys Tyr Tyr Ile Glu Gly Ile Asn Gln Leu Ser Cys Lys Cys
            20                  25                  30

Pro Asn Gly Phe Phe Gly Gln Arg Cys Gln Asn Tyr Val Met Ala Ser
        35                  40                  45

Phe Tyr
    50

<210> SEQ ID NO 29
<211> LENGTH: 52
<212> TYPE: PRT
<213> ORGANISM: artificial
<220> FEATURE:
<223> OTHER INFORMATION: hybrid polypeptide
```

```
<400> SEQUENCE: 29

Thr Asp His Glu Glu Pro Cys Gly Pro Ser His Lys Ser Phe Cys Leu
1               5                   10                  15

Asn Gly Gly Leu Cys Tyr Val Ile Pro Thr Ile Pro Ser Pro Phe Cys
            20                  25                  30

Lys Cys Pro Asn Gly Phe Phe Gly Gln Arg Cys Gln Asn Tyr Val Met
            35                  40                  45

Ala Ser Phe Tyr
    50
```

CHIMERIC NEUREGULINS AND METHOD OF MAKING AND USE THEREOF

This application is a continuation application of U.S. patent application Ser. No. 13/627,555, filed on Sep. 26, 2012. The entirety of the aforementioned application is incorporated herein by reference.

FIELD

This application generally relates to compositions containing a chimeric neuregulin and methods for prevention and treatment of neuronal and vascular damages with chimeric neuregulins.

BACKGROUND

Neuregulins are a family of multipotent growth factors that includes acetylcholine receptor inducing activities (ARIAS), growth factors, heregulins, and neu differentiation factors. Neuregulins' effects appear to be mediated by interaction with a class of tyrosine kinase receptors related to the epidermal growth factor receptor. Neuregulins stimulate the tyrosine phosphorylation of these receptors and the subsequent activation of various signal transduction mechanisms. Neuregulins are synthesized as transmembrane precursors consisting of either an immunoglobulin-like or cysteine-rich domain, and EGF-like domain a transmembrane domain and acytoplastic tail. Neuregulins have been known to be involved in the survival and function of neuronal cells. Neuregulin is also expressed in vascular endothelial cells and its receptors are localized in the underlying smooth muscle cells.

SUMMARY

One aspect of the present application relates to a chimeric neuregulin polypeptide having an integrin domain that binds to an integrin and an Erb3/4 binding domain that binds to Erb3 and/or Erb4. The chimeric neuregulin polypeptide comprises a neuregulin backbone derived from a native neuregulin polypeptide, and a donor fragment of at least one amino acid, wherein the donor fragment (1) replaces a target fragment in the native neuregulin polypeptide, wherein the donor fragment differs from the target fragment by at least one amino acid, or (2) is inserted into an insertion site of the native neuregulin polypeptide, and wherein the donor fragment forms at least a portion of the integrin binding domain and/or at least a portion of the Erb3/4 binding domain of the chimeric neuregulin polypeptide.

Another aspect of the present application relates to a chimeric neuregulin, comprising: a first moiety of at least 10 amino acids, wherein the first moiety is derived from a first polypeptide; and a second moiety of at least 5 amino acids, wherein the second moiety is derived from a second polypeptide; wherein the first polypeptide is a neuregulin and wherein the chimeric neuregulin exhibits an enhanced binding affinity to integrin, Erb 3, or Erb 4 comparing to that of the neuregulin.

Another aspect of the present application relates to a pharmaceutical composition comprising the chimeric neuregulin of the present application and a pharmaceutically acceptable carrier.

Another aspect of the present application relates to a method for ameliorating neuronal damage in a subject. The method comprises administering to the subject an effective amount of the pharmaceutical composition of the present application.

Another aspect of the present invention relates to a method for preventing or ameliorating secondary neuronal injury and inflammation following traumatic brain injury (TBI). The method comprises administering into a subject in need of such treatment an effective amount of the pharmaceutical composition of the present application.

Another aspect of the present invention relates to a method for ameliorating blood vessel damage caused by acute mechanical or chemical assault in a subject. The method comprises administering to said subject an effective amount of the pharmaceutical composition of the present application.

Other aspects of the invention will become apparent to the skilled artisan by the following description of the invention.

BRIEF DESCRIPTION OF THE DRAWINGS

The invention of this application is better understood in conjunction with the following drawing, in which:

FIG. 2 shows the consensus sequences of NRG1, NRG2, NRG3 and NRG4.

FIG. 3 shows the amino acid sequences of certain chimeric neuregulin.

FIGS. 4A-4F are pictures showing ErbB4 receptor expression in apoptotic and degenerating neurons. After ErbB4 immunohistochemistry, brain sections from rats MCAO were stained with Fluoro-Jade, a marker for degenerating neurons. Many neurons in the cortex were Fluoro-Jade-positive (FIG. 4A). ErbB4 positive cells (FIG. 4B) were co-localized in Fluoro-Jade-positive neurons (FIG. 4C). Similarly, TUNEL staining (FIG. 4D) and ErbB4 (FIG. 4E) were double-labeled (FIG. 4F) in a subpopulation of cells in the ipsilateral brain. Arrows indicate examples of double-labeled cells. Scale bar is 40 µM in panels A-C and 20 µM in FIGS. 4D-4F.

FIGS. 5A-5D are pictures showing ErbB4 expression in macrophages/microglia but not astrocytes following MCAO. Sections from the ipsilateral hemisphere were double labeled with antibodies against ErbB4 (FIG. 5A) and GFAP (FIG. 5B). Cells in the peri-infarct regions did not show co-localization of ErbB4 and GFAP (FIG. 5C). Co-localization of ErbB4 and Mac-1/CD11b indicated that ErbB4 is found in a subset of macrophages/microglia (FIG. 5D). (Double arrows indicate examples of double labeled cells). Scale bar is 40 µM in panel A-C and 20 µM in FIG. 5D.

FIGS. 6A-6D are pictures and graphs showing that NRG1β treatment reduce MCAO/reperfusion-induced brain infarction. Representative 2,3,5-triphenyltetrazolium chloride (TTC) stained brain sections are shown from rats injected with vehicle (FIG. 6A; n=11), NRG-1β (FIG. 6B; n-7) or NRG-1α (FIG. 6C; n=3) before MCAO. Infarct volumes in brains from vehicle and NRG-1 treated animals are shown in the graph (FIG. 6D). Values are presented as mean±SEM; * denotes significantly different from respective vehicle treated animals (P<0.01).

DETAILED DESCRIPTION

Figure 1:
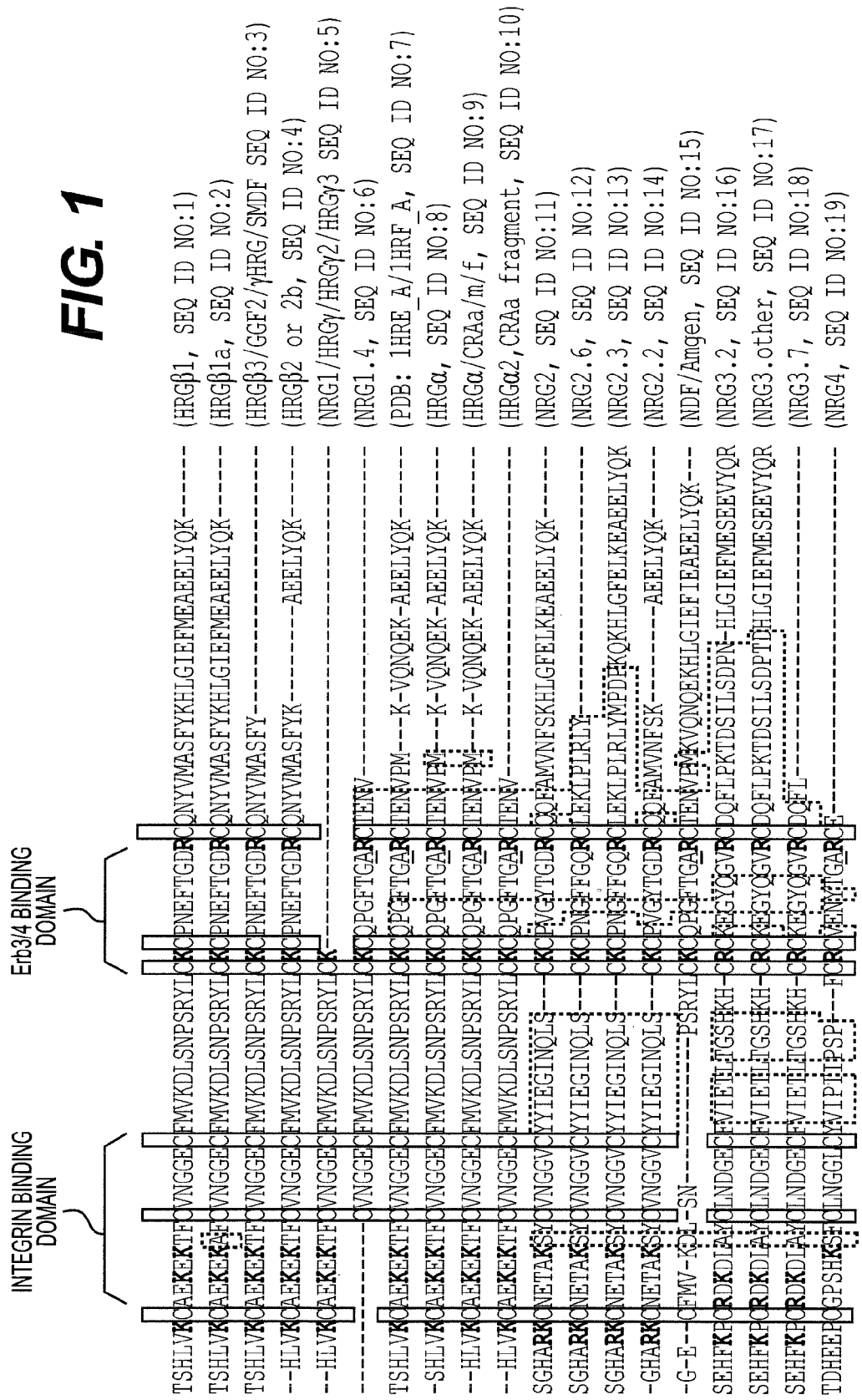
FIG. 1 is a protein sequence alignment of the integrin binding domain and Erb3/4 binding domain of various neuregulins.

The present invention relates to chimeric neuregulins, methods of making chimeric neuregulins, and methods and compositions for prevention and treatment of neuronal and vascular damages with chimeric neuregulins.

Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

The term "neuregulin" as used herein, refers to a family of proteins that includes: neuregulin-1 (NRG1), neuregulin-2 (NRG2), neuregulin-3 (NRG3), and neuregulin-4 (NRG4). Neuregulin-1, which has also been described in the literature as acetylcholine receptor inducing activity (ARIA), glial growth factor (GGF), glial growth factor 2 (GGF2); heregulin and neu differentiation factor (NDF); sensory and motor neuron-derived factor (SMDF), HGL; HRG; HRG1; HRGA and MST131, further contains a number of isoforms that include type I NRG1, type II NRG1, type III NRG1, type IV NRG1, type V NRG1 and type VI NRG1. The term "NRG1," as used herein, also includes all other NRG1 isoforms. NRG1 isoforms are synthesized as transmembrane precursors consisting of either an immunoglobulin-like or cysteine-rich domain, an EGF-like domain, a transmembrane domain and a cytoplasmic tail (Fischbach et al., Annu Rev Neurosci, 1997. 20:429-58). NRG1 isoforms are generated from one gene by alternative mRNA splicing, and most of them are synthesized as part of a larger transmembrane precursor. The two major classes of NRG1 include α and β isoforms. The NRG1β isoforms predominate in the nervous system, while α isoforms are prevalent in mesenchymal cells. The β isoforms are 100 to 1,000 fold more potent in stimulating AChR synthesis in skeletal muscle and Schwann cell proliferation (Buonanno et al., Curr Opin Neurobiol, 2001. 11:287-96). The effects of NRG1 appear to be mediated by interaction with a class of tyrosine kinase receptors related to the epidermal growth factor (EGF) receptor which includes ErbB2, ErbB3 and ErbB4 (Burden et al., Neuron, 1997. 18:847-55). The EGF-like domain of NRG1 appears to be sufficient for activation of ErbB receptors and downstream signal transduction pathways (Holmes et al., Science, 1992. 256:1205-1210). NRG1 stimulates the tyrosine phosphorylation of these receptors and the subsequent activation of various signal transduction mechanisms including Map kinase, PI3 kinase and CDK5 (Fu et al., Nat Neurosci, 2001. 4:374-81).

Neuregulin 2 (NRG2) is a novel member of the neuregulin family of growth and differentiation factors. Through interaction with the ErbB family of receptors, NRG2 induces the growth and differentiation of epithelial, neuronal, glial, and other types of cells. The gene consists of 12 exons and the genomic structure is similar to that of neuregulin 1 (NRG1). NRG1 and NRG2 mediate distinct biological processes by acting at different sites in tissues and eliciting different biological responses in cells. The NRG2 gene is located close to the region for demyelinating Charcot-Marie-Tooth disease locus, but is not responsible for this disease. Alternative transcripts encoding distinct isoforms have been described (Chang, H., et al. Nature (1997) 387: pp. 509-12; Carraway, K L, et al. Nature (1997) 387: pp. 512-16).

Neuregulin 3 (NRG3) binds to the extracellular domain of the ERBB4 receptor tyrosine kinase but not to the related family members ERBB2 or ERBB3. NRG3 binding stimulates tyrosine phosphorylation of ERBB4. Variants of the NRG3 gene have been linked to a susceptibility to schizophrenia (Zhang D, et al. Proc. Natl. Acad. Sci. U.S.A. (1997) 94: pp. 9562-7; Chen, P L, et al. Am. J. Hum. Genet. (2009) 84: pp. 21-34).

Neuregulin 4 (NRG4) activates type-1 growth factor receptors (EGFR) to initiating cell-to-cell signaling through tyrosine phosphorylation. Loss of expression of NRG4 is frequently seen in advanced bladder cancer while increased NRG4 expression correlates to better survival (Haran, D., et al. Oncogene (1999) 18: pp. 2681-9); (Memon, A A., et al., Br. J. Cancer (2004) 91: pp. 2034-41)).

Examples of human neuregulin sequences include, but are not limited to, those listed under GenBank Accession Nos: ADN85612.1, AAF28851.1, AAF28850.1, AAF28849.1, AAF28848.1, ABR13844.1, ABR13843.1, EAW63417.1, EAW63416.1, EAW63415.1, AAI50610.1, ABQ53540.1, DAA00042.1, DAA00041.1, EAW62087.1, EAW62086.1, EAW62085.1, EAW62084.1, EAW62082.1, EAW62081.1, ADK90032.1, ADK90031.1, ADK90030.1, ADK90029.1, ADK90026.1, ADK90024.1, ADK90022.1, AAF28853.1, AAF28852.1, BAG70289.1, BAG70145.1, ABR13842.1, ABG77979.1, DAA00045.1, EAW63419.1, EAW63412.1, EAW63410.1, EAW63409.1, EAW63408.1, ADN85613.1, AA136812.1, ABQ53539.1, DAA00048.1, DAA00047.1, EAW62083.1, EAW62078.1, ADK90028.1, ADK90027.1, ADK90025.1, ADK90023.1, ADK90021.1, ADK90020.1, AAH73871.1, ABY66350.1, EAW99228.1, EAW99227.1, EAW62080.1, EAW62079.1, EAW63418.1, EAW63414.1, EAW63413.1, EAW63411.1, EAW63407.1, EAW80374.1, AAH64587.1, AAH06492.1, AA049724.1, AAH07675.1, AAP36053.1, AAH17568.1, CAI15622.1, CAH73645.1, CAH70641.1, CA117213.1, CAH71050.1, AAM71141.1, AAM71140.1, AAM71139.1, AAM71138.1, AAM71137.1, AAM71136.1, AAM71135.1, AAM71134.1, AAM71133.1, CAI22410.1, ABQ53543.1, ABQ53542.1, ABQ53541.1, DAA00046.1, DAA00044.1, DAA00043.1, DAA00040.1, CAL35830.1, CAL35831.1, CAL35829.1, BAD97155.1, NP_001159445.1, NP_001159444.1, NP_001010848.2, NP_004874.1, NP_053585.1, NP_001171864.1, NP_053586.1, NP_053584.1, Q02297.3, NP_001153467.1, NP_039258.1, NP_039251.2, NP_001153473.1, NP_001153471.1, NP_039250.2, NP_001153476.1, NP_612640.1, NP_039254.1, NP_001153468.1, NP_039256.2, NP_001153480.1, 014511.1, Q9H013.3, Q7RTV8, NP_039252.2, NP_001153479.1, NP_001153474.1, NP_001153477.1, NP_004486.2, NP_039253.1, P56975.1, AAA19954.1, AAA19953.1, AAA19951.1, AAA19950.1, AAB59358.1; AAB59622.1; AAI03985.2, AAI03985.2, AAI14335.2, AAI03984.2, Q8WWG1.1, AAA58640.1, AAA58639.1, AAA58638.1, AAC51756.1, AAY17216.1, 1910316A, ABY70644.1, ABY66349.1, ABY66348.1, ABC69293.1, AAA19952.1; AAA19955.1; AAA58641.1; AAB59358.1; AAB59622.1; AAC41764.1; AAH73871.1; AA114334.2; AAI36812.1; AA049724.1; AAP36053.1; ABC69293.1; ABQ53539.1; ABQ53540.1; ABR13843.1; ABR18344.1; ABY66350.1; BAA23417.1; BAD97155.1; BAF83419.1; BAF82616.1; BAG54044.1; BAG53780.1; BAG59183.1; BAH11473.1; BAH11479.1; BAH12729.1; CAD98015.1; CAG29284.1; CAH18333.1

The term "integrin binding domain of a NRG" or "integrin binding domain of an NRG consensus sequence," as used herein, refers to the amino acid sequence in a native neuregulin that is located between and including the first and the third cyctienes of the NRG consensus sequence shown in FIGS. 1 and 2.

The term "Erb3/4 binding domain of a NRG" or "Erb3/4 binding domain of an NRG consensus sequence," as used herein, refers to the amino acid sequence in a native neuregulin that is located between and including the last two cyctienes residues (i.e., the fifth and sixth cyctienes) of the NRG consensus sequence shown in FIGS. 1 and 2.

The term "non-neuregulin polypeptide," as used herein, refers to a polypeptide that is not a member of the neuregulin family.

The term "polypeptide" refers to a polymer in which the monomers are amino acid residues which are joined together through amide bonds. The terms "polypeptide" or "protein" as used herein are intended to encompass any amino acid sequence and include modified sequences such as glycoproteins. The term "polypeptide" is specifically intended to cover naturally occurring proteins, as well as those which are recombinantly or synthetically produced. The term "fragment," in reference to a polypeptide, refers to a portion (that is, a subsequence) of a polypeptide. A fragment contains at least three amino acids residues. In some embodiments, the fragment contains at least 5 or 10 amino acids residues. Orientation within a polypeptide is generally recited in an N-terminal to C-terminal direction, defined by the orientation of the amino and carboxy moieties of individual amino acids. Polypeptides are translated from the N or amino-terminus towards the C or carboxy-terminus.

The term "derived from" refers to the origin of a fragment or a polypeptide. A fragment or polypeptide is deemed to be "derived from" a protein if the amino acid sequence of the fragment or the polypeptide is identical to the amino acid sequence of the protein, or a portion or portions of the amino acid sequence of the protein. For example, a polypeptide with a sequence of HHHHKKK is deemed to be derived from a polypeptide with a sequence of HHHHCCCKKK.

"Solubility" is a measure the amount of a substance, in the context of this disclosure, a polypeptide, that will dissolve in a given amount of another substance, usually a liquid. Thus, an increase in solubility is an increase in the amount of a the polypeptide that remains without aggregating or separating from the substance (e.g., liquid) in which it is dissolved.

When referring to a polypeptide, "stability is a measure of the polypeptide's resistance to degradation. Thus, an increase in stability reflects an increase in the ability of the polypeptide to withstand degradation, for example, measured as an increased half-life in vivo, or an increased shelf life in vitro.

The term "enhanced binding affinity" is a relative term that refers to an binding affinity that is at least 50%, 100% or 200% above a baseline binding affinity. For example, if the binding affinity between an integrin and a chimeric neuregulin is more than 150% of the binding affinity between the same integrin and a native neuregulin (i.e., an over 50% increase in binding affinity), the chimeric neuregulin has an "enhanced binding affinity" to the integrin with regard to the native integrin.

The term "reduces" is a relative term, such that an agent reduces a response or condition if the response or condition is quantitatively diminished following administration of the agent, or if it is diminished following administration of the agent, as compared to a reference agent. Similarly, the term "prevents" does not necessarily mean that an agent completely eliminates the response or condition, so long as at least one characteristic of the response or condition is eliminated. Thus, a composition that reduces or prevents an infection or a response, such as a pathological response, can, but does not necessarily completely eliminate such an infection or response, so long as the infection or response is measurably diminished, for example, by at least about 50%, such as by at least about 70%, or about 80%, or even by about 90% of (that is to 10% or less than) the infection or response in the absence of the agent, or in comparison to a reference agent.

The term "subject" refers to an individual. Preferably, the subject is a mammal such as a primate, and, more preferably, a human. The term "subject" can include domesticated animals, such as cats, dogs, etc., livestock (e.g., cattle, horses, pigs, sheep, goats, etc.), and laboratory animals (e.g., mouse, rabbit, rat, guinea pig, etc.).

The term "treatment" or "treating" refers to administration of a composition to a subject with an undesired condition or at risk for the condition. The condition can be any pathogenic disease, autoimmune disease, cancer or inflammatory condition. The effect of the administration of the composition to the subject can have the effect of but is not limited to reducing the symptoms of the condition, a reduction in the severity of the condition, or the complete ablation of the condition.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed.

Chimeric Neuregulins

One aspect of the present invention relates to chimeric neuregulins that have improved biological activities or pharmacokinetic characteristics. The term "chimeric neuregulin," as used herein, refers to a polypeptide that comprises a sequence derived from a neuregulin polypeptide and a sequence derived from another polypeptide that can be a neuregulin or a non-neuregulin polypeptide.

In some embodiments, the chimeric neuregulin polypeptide has an integrin domain that binds to an integrin and an Erb3/4 binding domain that binds to Erb3 and/or Erb4. The chimeric neuregulin polypeptide comprises a neuregulin backbone derived from a native neuregulin polypeptide, and a donor fragment of at least one amino acid, wherein the donor fragment (1) replaces a target fragment in the native neuregulin polypeptide, wherein the donor fragment differs from the target fragment by at least one amino acid, or (2) is inserted into an insertion site of the native neuregulin polypeptide, and wherein the donor fragment forms at least a portion of the integrin binding domain and/or at least a portion of the Erb3/4 binding domain of the chimeric neuregulin polypeptide. In one embodiment, the chimeric neuregulin polypeptide has an enhanced binding affinity to integrin, Erb 3, or Erb 4, comparing to said native neuregulin peptide. In another embodiment, the donor fragment comprises a polypeptide derived from another neuregulin that is different from the native neuregulin. In another embodiment, the donor fragment comprises a polypeptide derived from a non-neuregulin. In another embodiment, the donor fragment comprises polypeptides derived from two neuregulins that are different from said native neuregulin. In another embodiment, the original neuregulin polypeptide is NRG2 or a fragment of NRG2, and the donor fragment comprises a polypeptide derived from NRG1β. In another embodiment, the native neuregulin polypeptide is NRG4 or a fragment of NRG4, and the donor fragment comprises a polypeptide derived from NRG1, or a polypeptide derived from NRG2, or both a polypeptide derived from NRG1 and a polypeptide derived from NRG2. In another embodiment, the chimeric neuregulin polypeptide further comprises a second donor fragment of at least one amino acid, wherein the second donor fragment (1) replaces a second target fragment in the native neuregulin polypeptide, wherein the second donor fragment differs from the second target fragment by at least one amino acid, or (2) is inserted into an insertion site of the native neuregulin polypeptide.

In other embodiments, the chimeric neuregulin comprises a first moiety of at least 10 amino acids, wherein the first moiety is derived from a first polypeptide; and a second moiety of at least 5 amino acids, wherein the second moiety is derived from a second polypeptide; wherein the first polypeptide is a neuregulin and wherein the chimeric neuregulin exhibits an enhanced binding affinity to integrin, Erb 3, or Erb 4 comparing to that of the neuregulin. In one embodiment, the second polypeptide is a neuregulin that is different from the first neuregulin. In another embodiment, the second polypeptide is a non-neuregulin polypeptide. In another embodiment, the chimeric neuregulin further comprises a third moiety derived from a third polypeptide. In a relevant embodiment, the third polypeptide is a neuregulin that is different from the native neuregulin. In another relevant embodiment, the second polypeptide is a second neuregulin and the third polypeptide is a third neuregulin, wherein the first neuregulin, second and third neuregulins are different from each other. In another embodiment, the first neuregulin is NRG2, and the second polypeptide is NRG1β. In another embodiment, the first neuregulin is NRG4 and the second polypeptide is NRG1 or NRG2. In another embodiment, the first moiety comprises a NRG integrin binding domain or a NRG Erb3/4 binding domain. In another embodiment, the first moiety comprises a NRG integrin binding domain, and the second moiety comprises a NRG Erb3/4 binding domain. In another embodiment, the first moiety comprises a NRG Erb3/4 binding domain and the second moiety comprises a NRG integrin binding domain.

In yet other embodiments, the chimeric neuregulin is a neuregulin polypeptide (the original neuregulin) in which a stretch of at least 5, 6, 7, 8 or 9 consecutive amino acid residues (the "original fragment") is replaced with a stretch of consecutive amino acid residues (the "donor fragment") from a donor polypeptide that is different from the original neuregulin polypeptide. The original neuregulin can be a full length neuregulin or a fragment of a neuregulin. The donor polypeptide can be another member of the neuregulin family or a non-neuregulin polypeptide. The donor fragment may have a length that is the same as, or is different from, the length of the original fragment. A chimeric neuregulin may contain more than one donor fragment. In one embodiment, one original fragment is replaced with two different donor fragments. In other embodiment, two original fragments are replaced with two different donor fragments. In a preferred embodiment, the original fragment comprises an integrin binding domain of a NRG consensus sequence or an Erb3/4 binding domain of a NRG consensus sequence.

In certain embodiments, the original neuregulin is NRG4 or a fragment of NRG4 and the donor fragment(s) is derived from NRG1 and/or NRG2. In other embodiments, the original neuregulin is NRG3 or a fragment of NRG3 and the donor fragment(s) is derived from NRG1 and/or NRG2. In other embodiments, the original neuregulin is NRG2 or a fragment of NRG2 and the donor fragment(s) is derived from NRG1 and/or NRG2. In yet other embodiments, the original neuregulin is NRG1 or a fragment of NRG1 and the donor fragment(s) is derived from NRG1 and/or NRG2. In one embodiment, the donor fragment is derived from NRG1β.

In certain embodiments, the chimeric neuregulin is a more effective Erb 3 or Erb 4 agonist than the original neuregulin polypeptide. In other embodiments, the chimeric neuregulin has a higher affinity to Erb 3 and/or Erb 4 than the original neuregulin. In other embodiments, the chimeric neuregulin has a higher affinity to integrin than the original neuregulin. Selection of the original neuregulin, the original fragment, the donor polypeptide and the donor fragment can be determined based on the sequence comparison and known Erb 3 and/or Erb 4 binding activity of the original neuregulin and the donor polypeptide.

For example, various neuregulins share the sequence homology shown in FIG. 1. Specifically, the neuregulin molecules all have a consensus sequence that contains six cystiene residues spread in a region that is involved in binding to integrine and Erb3/4 molecules (see, e.g., FIGS. 1 and 2). As shown in FIG. 1, NRG1, NRG2 and NRG3 all have either one or two positively charged amino acids (R, K or H) at the amino-end of the first cyctiene in the consensus sequence. NRGs with two positively charged amino acids (e.g., NRG2, NRG2.2, NRG 2.3 and NRG2.6) are able to bind integrins more effectively (i.e., having a higher affinity to integrins). There integrins are up-regulated on inflamed tissue or tumors.

Further, the affinities of various NRGs to Erb3/4 have been reported as follows:

NRG 1β>NRG1α>NRG4 (1/10 of NRG 1β)

NRG2>NRG3/NRG4 (1/10 the affinity of NRG2).

It thus appears that Erb3/4 interact with NRGs through the amino acid residues between the last two cyctienes in the consensus sequence, as well as the amino acid residues after the last cyctiene residue in the consensus sequence.

Therefore, NRG2s have the highest affinities for integrins but NRG1αs have highest affinities for Erb 3/4. Therefore, a chimeric neuregulin with the integrin binding domain of NRG2 and the Erb 3/4 binding domain of NRG1β would have similar affinities to integrin or Erb 3/4 when compared to NRG2 or NRG1β, respectively. However, such a chimeric neuregulin would have a greater potency to bind to both integrin and Erb3/4 when compared to NRG2 or NRG1β. For example, a NRG1/NRG2/NRG4 chimeric neuregulin would have the ability to tightly bind neurotropic or vascular integrins while preserving the chimeric's ability to bind and inhibit ErbB3 and ErbB4 signaling. FIG. 3 shows certain embodiments of chimeric neuregulins (SEQ ID NOS:20-29).

As used herein, a "variant of a chimeric neuregulin" is a chimeric neuregulin polypeptide that contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gin, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the desired bioactivity, secondary structure and hydropathic nature of the polypeptide.

A variant of a chimeric neuregulin preferably exhibits at least about 70%, more preferably at least about 80%, more preferably at least about 90% and most preferably at least about 95% homology to the original chimeric neuregulin polypeptide. Variants can be produced artificially using site directed or random mutagenesis, or by recombination of two or more preexisting variants. For example, a variant chimeric neuregulin polypeptide can include 1, or 2, or 5 or 10, or 15, or up to about 50 amino acid differences from the reference chimeric neuregulin.

Variants of chimeric neuregulin polypeptide also include polypeptides that are modified from the original chimeric neuregulin polypeptides by either natural process, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from post-translation natural processes or may be made by synthetic methods. Modifications include pegylation, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Methods of Producing Chimeric Neuregulins

The chimeric neuregulins or variants thereof may be produced using methods well known in the art. In certain embodiments, the chimeric neuregulins or variants thereof are produced by chemical synthesis. Briefly, a chimeric neuregulin may be synthesized by coupling the carboxyl group or C-terminus of one amino acid to the amino group or N-terminus of another. Due to the possibility of unintended reactions, protecting groups are usually necessary. Chemical peptide synthesis starts at the C-terminal end of the peptide and ends at the N-terminus. This is the opposite of protein biosynthesis, which starts at the N-terminal end.

In some embodiments, the chimeric neuregulines may be synthesized using traditional liquid- or solid-phase synthesis. Fmoc and t-Boc solid phase peptide synthesis (SPPS) can be employed to grow the peptides from carboxy to amino-terminus. In certain embodiments, the last "amino acid" added to the reaction is PEGylated. This last amino acid is often referred to as a carboxyl-PEG-amine, carboxyl-PEO-amine, or amine-PEG-acid, whereby the amine is blocked to protect against reaction and the acid is free to react with the amine group from the previously added amino acid in the reaction.

PEG (polyethylene glycol) and PEO (polyethylene oxide) are polymers composed of repeating subunits of ethylene glycol and ethylene oxide monomers. In one embodiment, a PEGylated GGF2/NRG2 chimeric (SEQ ID NO:28) would have the PEG moiety connected to the histidine residue (H) at the amino-terminus of the polypeptide. In one embodiment, the PEG moiety is 5 to 30 kDa in size. In another embodiment, the PEG moiety is 10 to 20 kDa in size.

In addition to using PEGylated end amino acid during synthesis, a chimeric neuregulin may be PEGylated by PEGylation. PEGylation is the process of covalent attachment of polyethylene glycol polymer chains to another molecule, normally a drug or therapeutic protein. PEGylation can be achieved by incubation of a reactive derivative of PEG with the target chimeric neuregulin. The covalent attachment of PEG to a chimeric neuregulin can "mask" the chimeric neuregulin from the host's immune system (reduced immunogenicity and antigenicity), increase the hydrodynamic size (size in solution) of the chimeric neuregulin which prolongs its circulatory time by reducing renal clearance. PEGylation can also provide water solubility to hydrophobic proteins.

The first step of the PEGylation is the suitable functionalization of the PEG polymer at one or both terminals. PEGs that are activated at each terminus with the same reactive moiety are known as "homobifunctional", whereas if the functional groups present are different, then the PEG derivative is referred as "heterobifunctional" or "heterofunctional." The chemically active or activated derivatives of the PEG polymer are prepared to attach the PEG to the desired molecule.

The overall PEGylation processes used to date for protein conjugation can be broadly classified into two types, namely a solution phase batch process and an on-column fed-batch process. The simple and commonly adopted batch process involves the mixing of reagents together in a suitable buffer solution, preferably at a temperature between 4 and 6° C., followed by the separation and purification of the desired product using a suitable technique based on its physicochemical properties, including size exclusion chromatography (SEC), ion exchange chromatography (IEX), hydrophobic interaction chromatography (HIC) and membranes or aqueous two phase systems.

The choice of the suitable functional group for the PEG derivative is based on the type of available reactive group on the molecule that will be coupled to the PEG. For proteins, typical reactive amino acids include lysine, cysteine, histidine, arginine, aspartic acid, glutamic acid, serine, threonine, tyrosine. The N-terminal amino group and the C-terminal carboxylic acid can also be used as a site specific site by conjugation with aldehyde functional polymers.

In certain embodiments, the PEG derivatives are produced by reacting the PEG polymer with a group that is reactive with hydroxyl groups, typically anhydrides, acid chlorides, chloroformates and carbonates. In other embodiments, more efficient functional groups such as aldehyde, esters, amides, etc. are made available for protein conjugation.

In certain embodiments, heterobifunctional PEGs are used for conjugation. These heterobifunctional PEGs are very useful in linking two entities, where a hydrophilic, flexible and biocompatible spacer is needed. Preferred end groups for heterobifunctional PEGs are maleimide, vinyl sulfones, pyridyl disulfide, amine, carboxylic acids and NHS esters.

In other embodiments, the pegylation agents contain branched, Y shaped or comb shaped polymers that show reduced viscosity and lack of organ accumulation.

In other embodiments, chimeric neuregulins or variants thereof are produced using recombinant DNA technologies. Procedures for the expression and purification of recombinant proteins are well established in the art.

In order to express a chimeric neuregulin is a biological system, a polynucleotide that encodes the chimeric neuregulin is constructed. In certain embodiments, the recombinant polynucleotide is codon optimized for expression in a selected prokaryotic or eukaryotic host cell, such as a mammalian, plant or insect cell. To facilitate replication and expression, the polynucleotide can be incorporated into a vector, such as a prokaryotic or a eukaryotic expression vector. Although the polynucleotide disclosed herein can be included in any one of a variety of vectors (including, for example, bacterial plasmids; phage DNA; baculovirus; yeast plasmids; vectors derived from combinations of plasmids and phage DNA, viral DNA such as vaccinia, adenovirus, fowl pox virus, pseudorabies, adenovirus, adeno-associated virus, retroviruses and many others), most commonly the vector will be an expression vector suitable for generating polypeptide expression products. In an expression vector, the polynucleotide encoding the neuregulin chimera is typically arranged in proximity and orientation to an appropriate transcription control sequence (promoter, and optionally, one or more enhancers) to direct mRNA synthesis. That is, the polynucleotide sequence of interest is operably linked to an appropriate transcription control sequence. Examples of such promoters include: the immediate early promoter of CMV, LTR or SV40 promoter, polyhedron promoter of baculovirus, *E. coli* lac or trp promoter, phage T7 and lambda $P_L$ promoter, and other promoters known to control expression of genes in prokaryotic or eukaryotic cells or their viruses. The expression vector typically also contains a ribosome binding site for translation initiation, and a transcription terminator. The vector optionally includes appropriate sequences for amplifying expression. In addition, the expression vectors optionally comprise one or more selectable marker genes to provide a phenotypic trait for selection of transformed host cells, such as dihydrofolate reductase or neomycin resistance for eukaryotic cell culture, or such as tetracycline or ampicillin resistance in *E. coli*.

The expression vector can also include additional expression elements, for example, to improve the efficiency of translation. These signals can include, e.g., an ATG initiation codon and adjacent sequences. In some cases, for example, a translation initiation codon and associated sequence elements are inserted into the appropriate expression vector simultaneously with the polynucleotide sequence of interest (e.g., a native start codon). In such cases, additional translational control signals are not required. However, in cases where only a polypeptide coding sequence, or a portion thereof, is inserted, exogenous translational control signals, including an ATG initiation codon is provided for expression of the chimeric neuregulin sequence. The initiation codon is placed in the correct reading frame to ensure translation of the polynucleotide sequence of interest. Exogenous transcriptional elements and initiation codons can be of various origins, both natural and synthetic. If desired, the efficiency of expression can be further increased by the inclusion of enhancers appropriate to the cell system in use.

Expression vectors carrying the chimeric neuregulins can be introduced into host cells by any of a variety of well-known procedures, such as electroporation, liposome mediated transfection, calcium phosphate precipitation, infection, transfection and the like, depending on the selection of vectors and host cells.

Host cells that contain chimeric neuregulins-encoding nucleic acids are, thus, also a feature of this disclosure. Favorable host cells include prokaryotic (i.e., bacterial) host cells, such as *E. coli*, as well as numerous eukaryotic host cells, including fungal (e.g., yeast, such as *Saccharomyces cerevisiae* and *Picchia pastoris*) cells, insect cells, plant cells, and mammalian cells (such as CHO cells). Recombinant chimeric neuregulin nucleic acids are introduced (e.g., transduced, transformed or transfected) into host cells, for example, via a vector, such as an expression vector. As described above, the vector is most typically a plasmid, but such vectors can also be, for example, a viral particle, a phage, etc. Examples of appropriate expression hosts include: bacterial cells, such as *E. coli, Streptomyces*, and *Salmonella typhimurium*; fungal cells, such as *Saccharomyces cerevisiae, Pichia pastoris*, and *Neurospora crassa*; insect cells such as *Drosophila* and *Spodoptera frugiperda*; mammalian cells such as 3T3, COS, CHO, BHK, HEK 293 or Bowes melanoma; plant cells, including algae cells, etc.

The host cells can be cultured in conventional nutrient media modified as appropriate for activating promoters, selecting transformants, or amplifying the inserted polynucleotide sequences. The culture conditions, such as temperature, pH and the like, are typically those previously used with the host cell selected for expression, and will be apparent to those skilled in the art.

In bacterial systems, a number of expression vectors can be selected depending upon the use intended for the expressed product. For example, when large quantities of a polypeptide or fragments thereof are needed for the production of antibodies, vectors which direct high level expression of fusion proteins that are readily purified are favorably employed. Such vectors include, but, are not limited to, multifunctional *E. coli* cloning and expression vectors such as BLUESCRIPT (Stratagene), in which the coding sequence of interest, e.g., a polynucleotide of the invention as described above, can be ligated into the vector in-frame with sequences for the amino-terminal translation initiating Methionine and the subsequent 7 residues of beta-galactosidase producing a catalytically active beta galactosidase fusion protein; pIN vectors (Van Heeke & Schuster (1989) J Biol Chem 264:5503-5509); pET vectors (Novagen, Madison Wis.), in which the amino-terminal methionine is ligated in frame with a histidine tag, and the like.

Similarly, in yeast, such as *Saccharomyces cerevisiae*, a number of vectors containing constitutive or inducible promoters such as alpha factor, alcohol oxidase and PGH can be used for production of the desired expression products. In mammalian host cells, a number expression systems, including both plasmids and viral-based systems, can be utilized.

A host cell is optionally chosen for its ability to modulate the expression of the inserted sequences or to process the expressed protein in the desired fashion. Such modifications of the protein include, but are not limited to, glycosylation, (as well as, e.g., acetylation, carboxylation, phosphorylation, lipidation and acylation). Post-translational processing for example, which cleaves a precursor form into a mature form of the protein (for example, by a furin protease) is optionally performed in the context of the host cell. Different host cells such as 3T3, COS, CHO, HeLa, BHK, MDCK, 293, WI38, etc. have specific cellular machinery and characteristic mechanisms for such post-translational activities and can be chosen to ensure the correct modification and processing of the introduced, foreign protein.

For long-term, high-yield production of recombinant chimeric neuregulin polypeptide, stable expression systems are typically used. For example, polynucleotides encoding a chimeric neuregulin polypeptides are introduced into the host cell using expression vectors which contain viral origins of replication or endogenous expression elements and a selectable marker gene. Following the introduction of the vector, cells are allowed to grow for 1-2 days in an enriched media before they are switched to selective media. The purpose of the selectable marker is to confer resistance to selection, and its presence allows growth and recovery of cells which successfully express the introduced sequences. For example, resistant groups or colonies of stably transformed cells can be proliferated using tissue culture techniques appropriate to the cell type. Host cells transformed with a nucleic acid encoding a chimeric neuregulin polypeptide are optionally cultured under conditions suitable for the expression and recovery of the encoded protein from cell culture.

Following transduction of a suitable host cell line and growth of the host cells to an appropriate cell density, the selected promoter is induced by appropriate means (e.g., temperature shift or chemical induction) and cells are cultured for an additional period. The secreted polypeptide product is then recovered from the culture medium. Alternatively, cells can be harvested by centrifugation, disrupted by physical or chemical means, and the resulting crude extract retained for further purification. Eukaryotic or microbial cells employed in expression of proteins can be disrupted by any convenient method, including freeze-thaw cycling, sonication, mechanical disruption, or use of cell lysing agents, or other methods, which are well know to those skilled in the art.

Expressed chimeric neuregulin polypeptides can be recovered and purified from recombinant cell cultures by any of a number of methods well known in the art, including ammonium sulfate or ethanol precipitation, acid extraction, anion or cation exchange chromatography, phosphocellulose chromatography, hydrophobic interaction chromatography, affinity chromatography (e.g., using any of the tagging systems noted herein), hydroxylapatite chromatography, and lectin chromatography. Protein refolding steps can be used, as desired, in completing configuration of the mature protein. Finally, high performance liquid chromatography (HPLC) can be employed in the final purification steps.

In certain examples, the nucleic acids are introduced into vectors suitable for introduction and expression in prokaryotic cells, e.g., *E. coli* cells. For example, a nucleic acid including a polynucleotide sequence that encodes a F2GF1 chimeric RSV antigen can be introduced into any of a variety of commercially available or proprietary vectors, such as the pET series of expression vectors (e.g., pET19b and pET21d). Expression of the coding sequence is inducible by IPTG, resulting in high levels of protein expression. The polynucleotide sequence encoding the chimeric RSV antigen is transcribed under the phage T7 promoter. Alternate vectors, such as pURV22 that include a heat-inducible lambda pL promoter are also suitable.

The expression vector is introduced (e.g., by electroporation) into a suitable bacterial host. Numerous suitable strains of *E. coli* are available and can be selected by one of skill in the art (for example, the Rosetta and BL21 (DE3) strains have proven favorable for expression of recombinant vectors containing polynucleotide sequences that encode F2GF1 chimeric RSV antigens.

In another example, a polynucleotide sequence that encodes a chimeric neuregulin is introduced into insect cells using a Baculovirus Expression Vector System (BEVS). Recombinant baculovirus capable of infecting insect cells can be generated using commercially available vectors, kits and/or systems, such as the BD BaculoGold system from BD BioScience. Briefly, the polynucleotide sequence encoding the chimeric neuregulin is inserted into the pAcSG2 transfer vector. Then, host cells SF9 (*Spodoptera frugiperda*) are co-transfected by pAcSG2-chimer plasmid and BD BaculoGold, containing the linearized genomic DNA of the baculovirus *Autographa californica* nuclear polyhedrosis virus (AcNPV). Following transfection, homologous recombination occurs between the pACSG2 plasmid and the Baculovirus genome to generate the recombinant virus. In one example, the chimeric neuregulin is expressed under the regulatory control of the polyhedrin promoter (pH). Similar transfer vectors can be produced using other promoters, such as the basic (Ba) and p10 promoters. Similarly, alternative insect cells can be employed, such as SF21 which is closely related to the SF9, and the High Five (Hi5) cell line derived from a cabbage looper, *Trichoplusia ni.*

Following transfection and induction of expression (according to the selected promoter and/or enhancers or other regulatory elements), the expressed chimeric polypeptides are recovered (e.g., purified or enriched) and renatured to ensure folding into a biologically active conformation.

In yet other embodiments, the chimeric neuregulins are expressed in vivo by a plasmid vector or a viral vector.

Methods for Treating Neuronal and Vascular Damages with Chimeric Neuregulin

One aspect of the present application relates to a method for ameliorating neuronal damage in a subject. The method includes administering to the subject an effective amount of a pharmaceutical composition comprising a chimeric neuregulin or a variant thereof, and/or an expression vector encoding a chimeric neuregulin or a variant thereof. The neuronal damage may be cause by an occlusive stroke, a neurotoxin, an acute CNS injury or traumatic brain injury (TBI).

Another aspect of the present application relates to a method for ameliorating secondary neuronal injury and inflammation following TBI in a subject. The method includes administering to the subject an effective amount of a pharmaceutical composition comprising a chimeric neuregulin or a variant thereof, and/or an expression vector encoding a chimeric neuregulin or a variant thereof Another aspect of the present application relates to a method for treating or ameliorating symptoms of neurodegenerative disorders. The method includes administering to a subject suffering from a neurodegenerative disorder an effective amount of a chimeric neuregulin or a variant thereof, and/or an expression vector encoding a chimeric neuregulin or a variant thereof. The term "neurodegenerative disorders" refer to diseases caused by progressive loss of structure or function of neurons, including death of neurons. Examples of neurodegenerative disorders include, but are not limited to, Alzheimer's disease, Parkinson's disease, Huntington's disease and amyotrophic lateral sclerosis.

While not to be bound by the theory, it is believed that administration of the chimeric neuregulin or variant thereof results in the mobilization and migration of endogenous neural stem cells (NSC) in vivo and can be used to stimulate adult neurogenesis.

The chimeric neuregulin may be administered by various routes, such as intrathecal administration, intravascular administration, intramuscular administration, subcutaneous administration, intraperitoneal administration, oral administration and topical administration. Preferably, the neuregulin is administered intrathecally.

In certain embodiments, the chimeric neuregulin is administered intrathecally in an amount sufficient to enhance migration of stem cells from the ventricle into damaged areas of the brain. The chimeric neuregulin may be administered via a shunt into the ventricle or subventricular zone or administered into the cerebral spinal fluid by injection at the lumbar region.

The use of shunts into the ventricle is well established practice in the medical community. Such shunts may be present for several day or weeks. While usually used to drain excess cerebral spinal fluid from the ventricle in cases of excessive production or blockage of flow, such shunts would be appropriate means for administration of chimeric neuregulin over a period of several weeks. The care of the shunt would be an ongoing responsibility of the medical team during the time the chimeric neuregulin is being administered to facilitate migration of the stem cells to areas of damage.

As used herein after "an effective amount of a chimeric neuregulin" is a mount that is required to confer a prophylactic or therapeutic effect on the treated subject, or an amount that is required to meliorate at least one symptom of a target disease or disorder in the treated subject. In certain embodiments, the chimeric neuregulin is used at an intrathecal dose range of 0.01 μg/kg body weight to 5 μg/kg body weight, 0.01 μg/kg body weight to 500 μg/kg body weight, 0.01 μg/kg body weight to 50 μg/kg body weight, 0.01 μg/kg body weight to 5 μg/kg body weight, 0.1 μg/kg body weight to 5 μg/kg body weight, 0.1 μg/kg body weight to 500 μg/kg body weight, 0.1 μg/kg body weight to 50 μg/kg body weight, 0.1 μg/kg body weight to 5 μg/kg body weight, 1 μg/kg body weight to 5 μg/kg body weight, 1 μg/kg body weight to 500 μg/kg body weight, 1 μg/kg body weight to 50 μg/kg body weight, 10 μg/kg body weight to 5 mg/kg body weight, 10 μg/kg body weight to 500 μg/kg body weight and 10 μg/kg body weight to 50 μg/kg body weight.

In other embodiments, the chimeric neuregulin is used at an intra-vascular or intramuscular dose range of 0.01 μg/kg body weight to 50 μg/kg body weight, 0.01 μg/kg body weight to 5 mg/kg body weight, 0.01 μg/kg body weight to 500 μg/kg body weight, 0.01 μg/kg body weight to 50 μg/kg body weight, 0.01 μg/kg body weight to 5 μg/kg body weight, 0.1 μg/kg body weight to 50 mg/kg body weight, 0.1 μg/kg body weight to 5 mg/kg body weight, 0.1 μg/kg body weight to 500 μg/kg body weight, 0.1 μg/kg body weight to 50 μg/kg body weight, 0.1 μg/kg body weight to 5 μg/kg body weight, 1 μg/kg body weight to 50 mg/kg body weight, 1 μg/kg body weight to 5 mg/kg body weight, 1 μg/kg body weight to 500 μg/kg body weight, 1 μg/kg body weight to 50 μg/kg body weight, 10 μg/kg body weight to 50 μg/kg body weight, 10 μg/kg body weight to 5 μg/kg body weight, 10 μg/kg body weight to 500 μg/kg body weight and 10 μg/kg body weight to 50 μg/kg body weight, 100 μg/kg body weight to 50 mg/kg body weight, 100 μg/kg body weight to 5 mg/kg body weight, 100 μg/kg body weight to 500 μg/kg body weight and 1 mg/kg body weight to 50 mg/kg body weight. Administration can be a single bolus dose or multiple bolus doses every day or every other day for a desired period of time (e.g., 5 days, 10 days, 15 days, 20 days, 25 days, 30 days or longer). The desired treatment period is determined by the health care provider based on the needs of each individual subject.

In certain embodiments, the chimeric neuregulin comprises an amino acid sequence selected from the group consisting of SEQ ID NOS:20-29. In certain other embodiments, the chimeric neuregulin is a PEGylated chimeric neuregulin. In other embodiments, the chimeric neuregulin is PEGlated at the N-terminal. In yet other embodiments, the PEG moiety in the PEGylated chimeric neuregulin has a molecular weight of 10-20 Kd.

In some embodiments, the chimeric neuregulin is used in a method for ameliorating neuronal damage of occlusive stroke. The method includes administering to a subject suffering from an occlusive stroke an effective amount of a chimeric neuregulin or a variant thereof, and/or an expression vector encoding a chimeric neuregulin or a variant thereof. In one embodiment, the chimeric neuregulin is administered after the onset of said occlusive stroke. In another embodiment, the chimeric neuregulin is administered within 24, 48 or 72 hours of the onset of said occlusive stroke. Preferably, the chimeric neuregulin is used in an amount that is effective in inhibiting inflammation in the subject. In certain embodiments, the chimeric neuregulin is administered in conjunction with a glutamate receptor inhibitor, a clot disrupting agent, such as t-PA, and/or other active agents. Examples of glutamate receptor inhibitors include, but are not limited to, dizocilpin maleate (MK 801), R-2-amino-5-phosphonopentanoate (AP5), 2-amino-7-phosphonoheptanoic acid (AP7), 3-[(R)-2-carboxypiperazin-4-yl]-prop-2-enyl-1-phosphonic acid (CPPene), PEAQX, Selfotel, Amantadine, Dextrallorphan, Dextromethorphan, Ethanol, Eticyclidine, Gacyclidine, Ibogaine, Ketamine, Magnesium, Memantine: Methoxetamine, Nitrous oxide, Phencyclidine, Rolicyclidine, Tenocyclidine, Methoxydine, Tiletamine, Xenon, Neramexane, Eliprodil, Etoxadrol, Dexoxadrol, WMS-2539, NEFA, Remacemide, Delucemine, 8A-PDHQ, Aptiganel (Cerestat, CNS-1102), HU-211, HU-210, Remacemide, Atomoxetine, and Rhynchophylline.

In certain other embodiments, the chimeric neuregulin is administered after the 72 hour window in an amount sufficient to enhance migration of stem cells from the ventricle into damaged areas of the brain. In some embodiments, the chimeric neuregulin is administered daily or every other day after the 72 hour window for 3-7, 3-14, 3-21 or 3-28 days.

The chimeric neuregulin may be administered by various routes, such as intravascular administration, intrathecal administration, intramuscular administration, subcutaneous administration, intraperitoneal administration, oral administration and topical administration. Preferably, the chimeric neuregulin is administered intra-arterially.

In certain embodiments, the chimeric neuregulin is administered intra-arterially in conjunction with a glutamate receptor inhibitor, a clot disrupting agent, and/or other active agents within 24, 48 or 72 hours of the onset of said occlusive stroke to ameliorate acute damage and, then administered intrathecally after the 72 hour window for 3-7, 3-14, 3-21 or 3-28 days in an amount sufficient to enhance migration of stem cells from the ventricle into damaged areas of the brain.

For purposes of regeneration of neuronal tissue, the administration of chimeric neuregulin should commence after the initial inflammation due to the assault has subsided. In certain embodiments, the administration of chimeric neuregulin is started within 3, 4, 5, 6 or 7 days or within 1, 2, 3 or 4 weeks or within 1, 2 or 3 months of the initial assault, and is administered daily or every other day or weekly for 1, 2, 3 4, 5 or 6 weeks. Because it is necessary for the stem cells that have migrated to be replenished in the ventricle, the intrathecal administration of chimeric neuregulin should not be repeated at less than one week intervals. Longer intervals may be appropriate in order to allow greater replenishment of the stem cell supply in the ventricle.

In a preferred embodiment, the chimeric neuregulin is administered using serum albumin as a carrier. In one embodiment, the chimeric neuregulin is administered arterially in 1% serum albumin. In certain embodiments, the chimeric neuregulin comprises a sequence selected from the group consisting of SEQ ID NOS:20-29. In certain other embodiments, the chimeric neuregulin is a PEGylated chimeric neuregulin.

The glutamate receptor inhibitor is used in an amount that is effective in blocking the excitotoxic events of ischemia and decrease damage to neuronal tissue and injury arising from reperfusion. In certain embodiments, the chimeric neuregulin and/or glutamate receptor inhibitor are administered via the carotid artery. In other embodiments, the chimeric neuregulin and/or glutamate receptor inhibitor are administered to a particular area via fluoroscopy guided catheter. Chimeric neuregulin may also be administered intravenously in conjunction with reperfusion therapy following occlusion of coronary arteries. In other embodiments, the chimeric neuregulin and/or glutamate receptor inhibitor are administered intrathecally. The chimeric neuregulin and glutamate receptor inhibitor may be administrated simultaneously or separately in any order.

In some other embodiments, the chimeric neuregulin is used in a method for ameliorating neuronal damage caused by exposure to neurotoxins, such as organophosphates. The method includes administering to a subject in need of such treatment an effective amount of a chimeric neuregulin or a variant thereof. In certain embodiments, the chimeric neuregulin or variant thereof is administered in conjunction with the administration of another active agent to ameliorate permanent damage from the neurotoxins. Examples of such active agents include, but are not limited to, antidotes to neurotoxin and anticonvulsants.

Examples of neurotoxins include, but are not limited to, organophosphates, ion channel inhibitors, insects and animal venoms. Examples of antidotes to neurotoxin include, but are not limited to, atropine, prostigmine glutamate antagonists, oximes and benzodiazepies.

In certain embodiments, the chimeric neuregulin and/or other active agent is given within 72 hours, preferably within 48 hours, more preferably within 24 hours, from the initial exposure to the neurotoxin. In other embodiments, the chimeric neuregulin and/or other active agent are administered intrathecally or via the carotid artery. In other embodiments, the chimeric neuregulin and/or other active agent are administered to a particular area via fluoroscopy guided catheter. Chimeric neuregulin may also be administered intravenously or intramuscularly. The chimeric neuregulin and other active agent may be administrated simultaneously or separately in any order.

In some other embodiments, the chimeric neuregulin is used in a method for ameliorating neuronal damage caused by neuronal cell death associated with CNS injury due to: Alzeimer's Disease, epilepsy, neonatal hypoxic ischemia, and seizures associated with traumatic brain injury, nerve agent exposure, ischemic stroke, hemorrhagic stroke, transient ischemic attacks, silent cerebral infarct, blunt force trauma. The method includes administering to a subject in need of such treatment an effective amount of a chimeric neuregulin or a variant thereof Another aspect of the present invention relates a method for preventing or ameliorating secondary neuronal injury and inflammation following traumatic brain injury (TBI). The method comprises the step of administering into a subject in need of such treatment an effective amount of a chimeric neuregulin or a variant thereof, or an expression vector encoding a chimeric neuregulin or a variant thereof.

In certain embodiments, the chimeric neuregulin and/or other active agent is given within 72 hours, preferably within 48 hours, more preferably within 24 hours of TBI. In other embodiments, the chimeric neuregulin and/or other active agent are administered intrathecally or via the carotid artery. In other embodiments, the chimeric neuregulin and/or other active agent are administered to a particular area via fluoroscopy guided catheter. Chimeric neuregulin may also be administered intravenously or intramuscularly. The chimeric neuregulin and other active agent may be administrated simultaneously or separately in any order.

In a preferred embodiment, the chimeric neuregulin is administered using serum albumin as a carrier. In one embodiment, the chimeric neuregulin is administered arterially in 1% serum albumin. In certain embodiments, the chimeric neuregulin comprises a sequence selected from the group consisting of SEQ ID NOS:20-29. In another embodiment, the chimeric neuregulin is a PEGylated chimeric neuregulin.

Another aspect of instant invention relates to a method for ameliorating blood vessel damage caused by acute mechanical or chemical assault. The method comprises the step of administering to a subject in need of such treatment an effective amount of a chimeric neuregulin or a variant thereof, or an expression vector encoding a chimeric neuregulin or a variant thereof. While not to be bound by the theory, it is believed that the chimeric neuregulin or variant thereof prevents damages arising from responses to invasive procedures by inhibiting mitogen-stimulated VSMC proliferation and migration.

In certain embodiments, the acute vascular conditions are caused by physical assault to the blood vessels, such as placement of a balloon or stent in the artery, diagnostic cardiac catheterization, and cardiac surgery, especially surgery on the heart valves. The neuregulin treatment provides protection from permanent damage to blood vessels from restenosis and artherosclerosis arising from such physical assault. In addition to administration of neuregulin by intravenous or intra-arterial route during or after the damaging occasion, a stent or catheter for use in an invasive procedure may be coated with neuregulin. Other routes, such as intramuscular injection, may also be used.

In certain embodiments, the chimeric neuregulin is used at an intravascular dose range of 0.01 µg/kg body weight to 50 mg/kg body weight, 0.01 µg/kg body weight to 5 mg/kg body weight, 0.01 µg/kg body weight to 500 µg/kg body weight, 0.01 µg/kg body weight to 50 µg/kg body weight, 0.01 µg/kg body weight to 5 µg/kg body weight, 0.1 µg/kg body weight to 50 m/kg body weight, 0.1 µg/kg body weight to 5 µg/kg body weight, 0.1 µg/kg body weight to 500 µg/kg body weight, 0.1 µg/kg body weight to 50 µg/kg body weight, 0.1 µg/kg body weight to 5 µg/kg body weight, 1 µg/kg body weight to 50 mg/kg body weight, 1 µg/kg body weight to 5 m/kg body weight, 1 µg/kg body weight to 500 µg/kg body weight, 1 µg/kg body weight to 50 µg/kg body weight, 10 µg/kg body weight to 50 mg/kg body weight, 10 µg/kg body weight to 5 m/kg body weight, 10 µg/kg body weight to 500 µg/kg body weight and 10 µg/kg body weight to 50 µg/kg body weight, 100 µg/kg body weight to 50 mg/kg body weight, 100 µg/kg body weight to 5 mg/kg body weight, 100 µg/kg body weight to 500 µg/kg body weight and 1 mg/kg body weight to 50 mg/kg body weight. Administration can be a single bolus dose or multiple bolus doses every day or every other day for a desired period of time (e.g., 5 days, 10 days, 15 days, 20 days, 25 days, 30 days or longer). The desired treatment period is determined by the health care provider based on the needs of each individual subject.

In a preferred embodiment, the chimeric neuregulin is administered using serum albumin as a carrier. In one embodiment, the chimeric neuregulin is administered arterially in 1% serum albumin. In certain embodiments, the chimeric neuregulin comprises a sequence selected from the group consisting of SEQ ID NOS:20-29. In another embodiment, the chimeric neuregulin is a PEGylated chimeric neuregulin. In other embodiments, the chimeric neuregulin is PEGlated at the N-terminal. In yet other embodiments, the PEG moiety in the PEGylated chimeric neuregulin has a molecular weight of 10-20 Kd.

Pharmaceutical Compositions

Another aspect of the present invention relates to a pharmaceutical composition for treating neurodegenrative disorder and preventing or ameliorating neuronal damage caused by occlusive stroke, neurotoxin or acute assault on vascular and neuronal tissue. The pharmaceutical composition contains a chimeric neuregulin or a variant thereof, and a pharmaceutically acceptable carrier. In certain embodiments, the neuregulin comprises a sequence selected from the group consisting of SEQ ID NOS:20-29.

As used herein the language "pharmaceutically acceptable carrier" is intended to include any and all solvents, solubilizers, fillers, stabilizers, binders, absorbents, bases, buffering agents, lubricants, controlled release vehicles, diluents, emulsifying agents, humectants, lubricants, dispersion media, coatings, antibacterial or antifungal agents, isotonic and absorption delaying agents, and the like, compatible with pharmaceutical administration. The use of such media and agents for pharmaceutically active substances is well-known in the art. See e.g., A. H. Kibbe Handbook of Pharmaceutical Excipients, 3rd ed. Pharmaceutical Press, London, UK (2000). Except insofar as any conventional media or agent is incompatible with the active compound, use thereof in the compositions is contemplated. Supplementary agents can also be incorporated into the compositions.

In certain embodiments, the pharmaceutically acceptable carrier comprises serum albumin.

The pharmaceutical composition of the invention is formulated to be compatible with its intended route of administration. Examples of routes of administration include parenteral, e.g., intrathecal, intra-arterial, intravenous, intradermal, subcutaneous, oral, transdermal (topical) and transmucosal administration. Solutions or suspensions used for parenteral, intradermal, or subcutaneous application can include the following components: a sterile diluent such as water for injection, saline solution, fixed oils, polyethylene glycols, glycerine; propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the injectable composition should be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the requited particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a neuregulin) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active, ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Stertes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the pharmaceutical compositions are formulated into ointments, salves, gels, or creams as generally known in the art.

In certain embodiments, the pharmaceutical composition is formulated for sustained or controlled release of the active ingredient. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from e.g. Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein includes physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. In certain embodiments, single dosage contains 0.01 ug to 50 mg of a chimeric neuregulin.

Kits

The invention also encompasses kits for treating or preventing neuronal damage caused by an occlusive stroke or exposure to neurotoxins, kits for treating neurodegenerative disorders, kits for treating or preventing blood vessel damage caused by acute mechanical or chemical assault, kits for treating or preventing acute CNS injuries, and kits for preventing or amelioratring secondary neuronal injury and inflammation following traumatic brain injury (TBI). The kits comprise one or more effective doses of a chimeric neuregulin, a variant of a chimeric neuregulin, an expression vector encoding a chimeric neuregulin or a variant of a chimeric neuregulin, or combinations thereof along with a label or labeling with instructions on using the chimeric neuregulin, the variant of chimeric neuregulin, or the expression vector according to the methods of the invention. In certain embodiments, the kits can comprise components useful for carrying out the methods such as devices for delivering the chimeric neuregulin, the variant of a chimeric neuregulin, or the expression vector. In certain other embodiments, the kits can further contain another active agent to be administered in conjunction with the chimeric neuregulin, the variant of chimeric neuregulin, or the expression vector.

EXAMPLES

Example 1

Prevention of Post-Trauma Damage to Blood Vessels with Neuregulin-1

The effect of NRG1 on neointimal formation following balloon injury to the carotid artery of the rat was examined. NRG1 (2.5 µg/kg) was administered by tail-vein injection prior to injury and every two days following injury. Two weeks after carotid artery injury, NRG1-treated animals demonstrated a 50% reduction in lesion size compared to controls receiving the vehicle. The effect of NRG1 on vascular smooth muscle cell (VSMC) function was studied. A7r5 rat VSMC cultures were pretreated with NRG1 for 24 hours, and then stimulated with platelet derived growth factor (PDGF) for 48 hours. NRG1 significantly decreased both baseline and PDGF-stimulated VSMC proliferation in a dose-dependent manner. NRG1 also blocked VSMC migration and prevented the downregulation of a-smooth muscle actin by PDGF, indicating that it may prevent VSMC phenotypic reversion following injury. These findings demonstrate NRG1 as a therapeutic agent for the treatment of restenosis and atherosclerosis.

Experimental Injury, Harvest, and Tissue Preparation of Rat Carotid Arteries

Male Sprague-Dawley rats (350-400 g) were balloon-injured using methods as previously described in accordance with a protocol approved by the Standing Committee on Animals, Morehouse School of Medicine. Rats were anesthetized with an intraperitoneal injection of xylazine (5 mg/kg body weight) and ketamine hydrochloride (90 mg/kg body weight). The left common carotid artery was exposed by a 6-cm midline cervical incision. Proximal and distal blood flow was occluded by clamping. Polyethylene 10 tubing was inserted retrogradely into the internal carotid artery and advanced into the left common carotid artery. After gentle flushing of the artery with normal saline, the tubing was removed and a 2-French (F) Fogarty embolectomy balloon catheter was inserted. Balloon inflation to 1.5 to 1.8 times the external diameter of the artery was achieved by caliper measurement under stereomicroscopy. After holding the inflation for 30 seconds, the catheter was removed. The uninjured right carotid artery was used as the control. Rats were treated with NRG1β or NRG-1α (EGF-like domain, R&D Systems, Minneapolis, Minn. dissolved in 1% BSA/PBS) by tail-vein administration at a dose of 2.5 ug/kg body weight, starting at day 0 before injury, and continuing for every 2 days for the next 14 days. Control rats were treated with vehicle (1% BSA/PBS). The animals were weighed before the procedure and at sacrifice to evaluate the possible adverse effects of NRG1. Vessels were harvested time points 0 and 14 days for mRNA analysis or histology. Injured vessels were compared with their contralateral controls.

Tissue Processing and Quantitative Histomorphometric Analysis

Animals were euthanized with $CO_2$ 14 days after injury. Carotid arteries were washed with saline to clear blood, embedded in Tissue-Tek OCT medium and frozen using liquid nitrogen. Carotid sections were cut with a cryostat into cross sections of 12 µm taken from the center and distal portion of the vessels, and stained with hematoxylin and eosin. The medial thickness was determined by the area of the internal elastic lamina subtracted from the external elastic lamina. Morphometry was performed using at least six individual sections of each arterial segment and used to determine the lesion size expressed as intima/media ratio. The intimal and medial layer thicknesses were measured using a computer-based image analyzing program (Image J, NIH).

A7r5 VSMC Cultures

A7r5 rat aortic vascular smooth muscle cells (VSMC) (ATCC CRL-1444) were obtained from American Tissue Type Culture (Manassas, Va.) and grown in Dulbecco's modified Eagle medium supplemented with glutamine, 10% fetal calf serum (FCS), and 1% Penicillin/Streptomycin at 37° C. in a humidified incubator with 5% $CO_2$. Cells were passaged weekly. All studies were performed on cells from passages 9-12.

Determination of VSMC Proliferation

VSMC were seeded at a density of $1 \times 10^3$ cells in triplicate wells of a 96 well plate. After 24 hours, cells were serum starved in DMEM/F-12 (Gibco; Carlsbad, Calif.) containing 0.1% FCS (low serum medium; LSM) to induce quiescence. After 24 hours of serum deprivation, cells were pretreated with 0-200 nM of NRG1α or NRG1β for 24 hours. Cells were then treated with 10 ng/mL of PDGF-BB for 48 hours to stimulate VSMC proliferation. For direct measure of cell number, cells were counted using a Coulter counter. VSMC cell proliferation and viability was also measured using the CellTiter 96 AQueous Non Radioactive Cell Proliferation Assay (Promega; Madison, Wis.) according to the manufacturer's protocol. After incubation at 37° C. in humidified 5% $CO_2$ for 1 hour, the absorbance was recorded at 490 nm using a plate reader. Measurement of DNA synthesis was performed using the BrDU Cell Proliferation Assay (Calbiochem, San Diego, Calif.) according to the manufacturer's protocol.

Cell Migration Assay

Neuro Probe 48-well microchemotaxis chambers (Costar, Corning Inc.) with PVP-free polycarbonate filter (8.0 µm pore size) were used to measure VSMC migration. Quiescent cells were trypsinized and resuspended in LSM with or without NRG1 and incubated for 24 hours at 37° C. Cells were then treated with PDGF which was added to the bottom well of the Boyden chamber and incubated for 48 hours at 37° C. Cells that migrated to the lower side of the filters were fixed and stained with the Diff Quick staining kit (VWR Laboratory, West Chester, Pa.). The filters were mounted on glass slides and counted by light microscopy using ×100 magnification.

Protein Purification and Western Analysis

Reactions were terminated by placing the cells on ice, aspirating the medium and adding ice-cold lysis buffer (50 mM Tris, 150 mM NaCl, 1 mM EDTA, 0.5% Triton X-100, 0.5% Nonidet P-40, 1 mM sodium orthovanadate, 1 mM phenyl methanesulfonyl fluoride, pH 8.0) for 30 minutes at 4° C. Harvested lysates were denatured with loading buffer, resolved in SDS/5% polyacrylamide gels and transferred to poly vinylidene difluoride (PVDF) membranes (Millipore Corp., Bedford, Mass.). Membranes were be blocked with 3% nonfat dry milk in phosphate buffered saline-0.5% Tween 20 (PBST) and exposed to primary antibody, anti-smooth muscle alpha-actin (SMA) (Santa Cruz, Ca.) diluted in blocking buffer overnight at 4° C. After incubation, membranes were washed with PBST. After wash, membranes were exposed to an alkaline phosphatase-conjugated anti-rabbit secondary antibody for 1 hour. Membranes were subsequently washed with PBST, incubated with chemiluminescence reagents and exposed to x-ray film. For ERK1/2 phosphorylation, VSMC were pre-treated with NRG1β for 24 hours and stimulated for 15 minutes with PDGF. Western blots were performed using primary antibodies for phosphorylated and unphosphorylated forms of ERK1/2 (Cell Signaling, Danvers, Mass.) diluted 1:250 in blocking buffer. Immunoblotting using an anti-tubulin antibody was used to normalize protein levels in each sample.

Cell Viability Assay

Quantitative viability assessment was performed using 1% Calcein-AM (Molecular Probes, Eugene, Oreg.), a fluorescent membrane-integrity dye, diluted in HBSS according to the manufacturer's protocol. Qualitative assessment of cell viability in treated cells was performed using the trypan blue-exclusion assay. Non-viable cells were quantified visually using a light microscopy.

Statistical Analysis

Each experiment was repeated a minimum of three times. Data are expressed as the mean±standard deviation (SD). An unpaired Student's t-test and ANOVA were performed to make comparisons between groups. A value of p less than 0.05 was considered significant.

NRG1 Attenuated Neointima Formation after Rat Carotid Balloon Injury

Neointimal hyperplasia was histologically evident in the carotid arteries 14 days after balloon injury compared to uninjured contralateral controls. The neointima of the rats receiving intravenous administration of NRG1 was significantly reduced compared to balloon-injured animals. Morphometric analysis showed that NRG1 reduced the size of the lesion by ~50% compared to vehicle-treated control animals. Treatment of animals with NRG1 showed no overt negative side effects and there was no significant difference in body weight observed among the control and NRG1 treated rats.

NRG1 Inhibits Proliferation in VSMC

Serum-starved VSMC were pre-treated with NRG1 for 24 hours, then stimulated with PDGF for an additional 48 hours. Stimulation of cells with PDGF increased proliferation of VSMC 2-fold. Pre-treatment with either NRG1β or NRG-1α resulted in a dose-dependent decrease in baseline and PDGF-stimulated proliferation as measured by MTS activity. Direct cell counting using Coulter counter demonstrated that NRG1 reduced PDGF-stimulated VSMC proliferation, but not baseline cell numbers. Analysis of BrDU incorporation revealed a similar pattern to the Coulter counter demonstrating that NRG1β significantly inhibited PDGF-induced proliferation, but did not alter baseline DNA synthesis.

Calcein-AM and trypan blue viability assays were carried out in cells pre-treated with NRG1 with or without PDGF. The calcein-AM assay demonstrated that treatment of VSMC with NRG1 does not alter cell viability. These results were corroborated using the trypan-exclusion assay, which revealed that less than 1.0% of the cells took up the dye.

NRG1 Decreases VSMC Migration

The migration of VSMC was measured using a transwell migration assay. VSMC were pretreated with 100 nM NRG1α or NRG1β, and then stimulated with 10 ng/ml of PDGF-BB for 48 hours. The results show that NRG1 alone does not alter baseline VSMC migration. VSMC treated with PDGF displayed a 2-3 fold increase in migration. Both NRG-1α and NRG-1β decreased PDGF-stimulated VSMC migration by 80% and 90%, respectively.

NRG1 Regulates Smooth Muscle α-Actin Expression

The mRNA and protein expression on SMA, and a marker for differentiated and contractile VSMC, after NRG1 treatment was examined. Serum-starved, quiescent VSMC displayed SMA expression, which was reduced after treatment with PDGF. NRG1β alone did not alter SMA mRNA or protein expression, however, pre-treatment of PDGF-stimulated VSMC with NRG1β resulted in SMA expression that returned to near baseline levels.

NRG1 Inhibits PDGF-Induced Phosphorylation of ERK1/2

This study demonstrated that NRG1 attenuates neointimal formation and vascular balloon injury. NRG1 reduced the size of the lesion by ~50% compared to vehicle-treated control animals. This finding clearly shows that NRG1 is useful in the prevention of vascular diseases such as restenosis and atherosclerosis. The NRG1 blocks PDGF-induced proliferation of VSMC in a dose-dependent manner. The inhibitory effects of NRG1 on VSMC proliferation were confirmed by direct cell counting and measuring DNA synthesis by BrDU incorporation. An intriguing observation was the difference in the effect of NRG1 on baseline VSMC proliferation using the MTS-based assay compared to the other methods. In the cell counting and BrDU approaches, PDGF increased VSMC proliferation was blocked by NRG1, however, baseline VSMC numbers were not altered. Using the MTS-based assay, a 50% decrease in baseline MTS activity was seen after NRG1 administration. Since the MTS assay measures metabolic activity, it is possible that NRG1 may prevent PDGF-stimulated proliferation by promoting VSMC differentiation, which could result in a decrease in metabolic activity and/or a reduction in the capability of PDGF to stimulate VSMC proliferation. That this is due to apoptosis resulting from treatment is unlikely since there was no evidence of increased dead or non-viable cells after neuregulin treatment.

Example 2

Combination Therapy for Preventing Permanent Neuronal Damage

In the case of prevention of damage resulting from exposure to neurotoxins, such as organophosphates, or as a result of obstructive stroke, such as that caused by an infarct, studies were done studying effect on permanent middle cerebral artery occlusion (pMCAO) using combination therapy. Studies were done giving dizocilpin maleate (MK-801 from Sigma), a glutamate receptor inhibitor which blocks the excitotoxic events of ischemia in combination with neuregulin within a therapeutic window of about 13.5 hours in the rat to decrease permanent neuronal damage. The therapeutic window in larger animals having a lower metabolism would be in the range of 0 to 72 yours. In the case of expected exposure to neurotoxins, the neuregulin could be administered in conjunction with antidotes. Other active agents which may be used in conjunction with neuregulin in the manner disclosed for use with MK-801 are selfotel, aptiganel, magnesium, acetylcholine, GABA agonists (clomethiazole, diazepam and other benzodiazepines) and serotonin agonists.

In the case of damage arising from exposure to neurotoxins such as organophosphate (OP) nerve agents, current post-exposure medical countermeasures against nerve agents (e.g. atropine, prostigmine glutamate antagonists, oximes (such as 20 pralidoxime chloride) and benzodiazepines) are useful in preventing mortality, but are not sufficiently effective in protecting the CNS from seizures and permanent injury. Therefore, new and more effective medical countermeasures against OP nerve agents are needed to facilitate better treatment that will prevent extensive, permanent nerve damage in survivors. Other agents that may be used to treat patients that have been exposed to neurotoxin include anticonvulsants.

In both instances of pMCAO and exposure to neurotoxins, neuregulin may be administered concurrently with the other active agents to ameliorate permanent damage from infarct disintegrators or nerve agent counteractants. In certain embodiments, neuregulin is given within a 72 hour widow after the initial exposure to the causative agent or the onset of occlusion of the blood supply, more preferably within 24 hours after the causal event.

In both instances where the neuregulin is given as combination therapy to prevent cerebral neuronal damage the neuregulin is administered into the carotid artery with an appropriate carrier. In animal studies, the neuregulin is administered in bovine serum albumin. In humans, a preferred carrier would be human serum to be administered within the first 72 hours, preferably within the first 24 hours, of the assault, whether chemical or physical. In the instance where the neuregulin is to prevent damage resulting from mechanical damage to a blood vessel, the neuregulin may be given intravenously in the usual carriers used for intravenous administration. Addressing the use of neuregulin simultaneously with other agents, studies were done on rats that had been subjected to left middle cerebral artery occlusion (MCAO).

Middle Cerebral Artery Occlusion

All surgical procedures were performed by sterile/aseptic techniques in accordance with institutional guidelines. Adult male Sprague-Dawley rats weighing 250-300 g were used for this study. Animals were subjected to left MCA occlusion. Rats were anesthetized with a ketamine/xylazine solution (10 mg/kg, MCA occlusion was induced by the intraluminal suture MCAO method as previously described (Belayev et al. 1996; Belayev et al. 1995). Briefly, the left common carotid artery (CCA) was exposed through a midline incision and was carefully dissected free from surrounding nerves and fascia. The occipital artery branches of the external carotid artery (ECA) were then isolated, and the occipital artery and superior thyroid artery branches of the ECA were coagulated. The ECA was dissected further distally. The internal carotid artery (ICA) was isolated and carefully separated from the adjacent vagus nerve, and the pterygopalatine artery was ligated close to its origin with a 6-0 silk suture. Then, a 40 mm 3-0 surgical mono filament nylon suture (Harvard Apparatus, Holliston, Mass.) was coated with poly-L-lysine with its tip rounded by heating near a flame. The filament was inserted from the external carotid artery (ECA) into the internal carotid artery (ICA) and then into the circle of Willis to occlude the origin of the left middle cerebral artery. The suture was inserted 18 to 20 mm from the bifurcation of the CCA to occlude the MCA. In the permanent MCAO (pMCAO), the suture was left in place for 24 hours prior to sacrificing the animal. In the transient MCAO (tMCAO) model, the nylon suture was withdrawn 1.5 hours following ischemia and the brain tissues were reperfused for 24 hours before sacrificing. To determine the effects of NRG1 on ischemic stroke, rats were injected intra-arterially with a single bolus 10 ul dose of vehicle (1% BSA in PBS) or NRG1 β (10 μmol/L NRG1 (EGF-like domain, R&D Systems, Minneapolis, Minn.) in 1% BSA in PBS) through a Hamilton syringe.

NRG1 or vehicle was administered by bolus injection into the ICA through ECA immediately before MCAO. MK-801 (0.5 mg/kg) was either administered IP immediately prior to NRG1 administration or co-administered IA simultaneously with NRG1. All NRG1 and vehicle treatment studies were performed in a double-blinded manner. Core body temperature was monitored with a rectal probe and maintained at 37° C. with a Homeothermic Blanket Control Unit (Harvard Apparatus) during anesthesia. Neurological score was determined in a double blinded fashion using a five-point neurological evaluation scale (Menzies et al. 1992) in rats treated with vehicle or NRG1 four hours after reperfusion. All animals were tested prior to surgery (controls) and after treatment with NRG1 or vehicle. Neurological function was graded on a scale of 0-4 (normal score 0, maximal deficit score 4). While intra-arterial injection into the carotid artery was used, fluoroscopic guided catheter-based therapy wherein the catheter is guided to the arteries which best access the damaged tissue is appropriate.

Measurement of Infarct Formation

Twenty-four hours after reperfusion, the animals were killed and the brain tissue was removed and sliced into 2.0 mm-thick sections. Brain slices were incubated in a 2% triphenyltetrazolium chloride (TTC) solution for 30 minutes at 3° C. and then transferred into a 4% formaldehyde solution for fixation. TTC, a colorless salt, is reduced to form an insoluble red formazan product in the presence of a functioning mitochondrial electron transport chain. Thus, the infarcted region lacks staining and appears white, whereas the normal non-infarcted tissue appears red. Infarct area of four slices of 2 mm coronal sections of each brain was calculated in a blinded manner by capturing the images with a digital camera. Rats showing tremor and seizure (which rarely occurred in this study) were excluded from studies of brain infarction to eliminate cerebral hemorrhage or brain trauma as potential variables in this study. Infarct volumes were analyzed by ANOVA; $P<0.05$ was regarded as significant.

The Effect of NRG1 on Neural Stem Cells (NSCs) Isolated from E11 Mouse Telencephalon The telencephalon of E11 mouse embryos were isolated and the dissociated cells cultured as neurosphere cultures. Cultures were treated with the EGF-like domain of neuregulin-1β (NRG1). The EGF-like domain contains the receptor binding portion of the molecule and has been shown to display all the known biological activities of the full-length neuregulins. The cells formed neurospheres and expressed nestin, an intermediate filament protein present in NSCs and RPs in the developing CNS. The cultures were examined to determine whether the addition of NRG1 to cell suspensions obtained from E11 mouse cortical tissue would generate neurospheres in the absence of bFGF. After 7 days in culture, there was no significant difference in the total number or size of neurospheres in the NRG1 treated group compared with the untreated group. This result demonstrated that NRG1 alone, unlike bFGF, could not generate neurospheres. When bFGF-generated neurospheres were plated onto coated coverslips in the presence of bFGF, cells continued to divide and migrate out of the sphere to form a monolayer. Upon withdrawal of bFGF, migrating cells differentiated into cells expressing neuronal, astrocyte and oligodendrocyte markers. Neuronal cells were identified by labeling with the anti-MAP2 antibody. Oligodendrocytes were identified with an antibody directed against O4 and astrocytes were identified with an antibody directed against GFAP. Morphologically, these MAP2-positive cells appeared neuronal and showed: (i) a spherical, ovoid, or pyramidal shaped soma; (ii) phase-bright appearance; (iii) branching processes (presumably dendrites) arising from the soma.

NRG1 Increases the Proliferation of MAP2-positive Cells in Neurosphere Cultures

The actions of NRG1 on βFGF-generated neurospheres were examined by plating neurospheres on coverslips as described above. Neurospheres were cultured in the absence or presence of 5 nM NRG1 for 5 days, and then, co-labeled with BrDU and MAP2 or GFAP antibodies. After 5 days of treatment with 5 nM NRG1, a dramatic increase in the number of cells surrounding the core of the neurosphere was observed in NRG1 treated cultures as compared to control. A 44±3.3% increase in [3H]thymidine incorporation was seen in NRG1 treated cultures that paralleled the increase in the total number of cells. More MAP2 and BrDU co-labeled cells were found both in the central core and peripheral area of NRG1 treated neurospheres, but few double-labeled cells were seen in the control. There was a 2.5-fold increase in MAP2 positive cells, but no increase in MAP2-negative cells, suggesting that the majority of NRG1 treated cultures were neuronal.

To further characterize the effect of NRG1 on NSCs, neurospheres were cultured in the absence or presence of 1 or 5 nM NRG1, then co-labeled with BrDU and MAP2 or GFAP antibodies. After 5 days, there was a 4-fold increase in the number BrDU-labeled cells in the neurosphere outgrowth area in 5 nM NRG1 treated group compared to control. A smaller, but significant increase was also observed with 1 nM NRG1 treatment demonstrating a dose-dependent response of cells to NRG1. Most of the BrDU positive cells co-labeled with the MAP2, but not the GFAP antibody. Therefore, the increased proliferation was specific for neuronal cells and not in GFAP-positive astrocytes. The increase in number of MAP2 positive cells that co-labeled with BrDU was parallel to the increase of BrDU positive cells, suggesting that most of the cells proliferating in response to NRG1 were neuronal. In cultures maintained for 8 days after withdrawal of bFGF, virtually no cells showed BrDU incorporation in control cultures. By that time point, most cells had differentiated and lost the ability to proliferate. However, numerous BrDU-positive neurons were present in the NRG1 treated group, suggesting that NRG1 prolongs the proliferation of immature neuronal cells. Under our culture conditions, few cells were labeled with GFAP and O4 in control cultures, or after treatment with NRG1, therefore the cells that labeled with BrDU alone were likely undifferentiated NSCs.

NRG1 Increases Proliferation Rather than Survival

The increased production of neurons could be altered by affecting (1) the proliferation of NRPs (2) the differentiation of NSCs into neurons, or (3) or by altering the survival of neuronal cells. Increased proliferation might result in an increase in the total number of cells as well as in the number of proliferating MAP2-positive cells; increased differentiation might result in an increase in the number of MAP2-positive cells within the same total population of cells; increased survival might result in an increase in MAP2-positive cells, but not necessarily cells co-labeled with BrDU or nestin. To determine whether the increase in the number of NRPs induced by NRG1 was due to the increase of cell survival, we evaluated cell viability by using a Viability. Assay Kit (Molecular probes). Results showed that the total number of cells increased after 4 days in the cultures. The number of live cells was greater in NRG1 treated group compared to control. Twice as many live cells were present in the NRG1 group after 8 days. There was no difference in the number of dead cells in control or NRG1 treated cultures at most time points. This result shows that NRG1 stimulated proliferation rather than cell survival.

NRG1 Stimulates the Mobilization of NSCs in Adult Rat Brain In vivo

SVZ cells were labeled by stereotaxically injecting DiI into the lateral ventricle of adult rats. Twenty-four hours later, NRG1 or vehicle were injected into the lateral ventricle and the animals were sacrificed 1 day later. Intense labeling was visible in the cells lining the ventricle (V) and in the choroids plexus (CP) after injection of DiI. When the vehicle was injected 24 after the DiI labeling, few cells had migrated out from the SVZ. However, after NRG1 administration, numerous NSCs had migrated from the SVZ, as far away as to the cerebral cortex. Similar results were seen when Fluorogold was injected into the lateral ventricle. Preliminary results indicate that a subpopulation of the labeled cells co-label with an antibody for NeuN, a neuronal marker.

The poor regenerative capacity of the sensory of the mammalian CNS has led to investigations of different approaches to increase the function of these structures after neurodegeneration or injury. One strategy to repair the injured CNS has been to replace the lost neurons with embryonic stem cell-derived neuronal stem cells (eNSCs). The use of eNSCs has shown promise in the treatment of a variety of neurological diseases and they have recently been shown to survive and differentiate into glia and neurons after CNS transplantation. However, a number of biological and ethical issues have slowed this area of research. NSCs have been demonstrated in the adult brain and have been shown to have the potential to differentiate into a variety of neuronal cell types. Therefore, another strategy has focused on maximizing the potential of this endogenous population of cells by stimulating their mobilization, proliferation, migration and differentiation in vivo following CNS injury and degeneration. Understanding the technical and logistic considerations for employing adult NSCs is essential to optimizing and maintaining cell survival before and after activation, as well as for tracking the fate of mobilized cells. It is now recognized that NSC strategies will be effective only if the new cells have the same abilities and characteristics as the original neurons. The administration of NRG1 into the cerebral spinal fluid or through a shunt into the ventricle for repeated administration (intrathecal administration) gives a method of encouraging production of stem cells in the ventricle with migration of stem cells from the ventricle to the damaged areas of the brain. Administration may be used with spinal tap or may be administered through a shunt into the ventricle. Appropriate carriers include glucose, isotonic glucose and other carriers usually used for intrathecal administration. However, the neuregulin may be administered into the cerebral spinal fluid at the lumbar region. For arterial administration, the carrier may, advantageously, contain serum albumin.

To obtain maximum benefit, the neuregulin will usually administer into the carotid artery or by some other means such as fluoroscopy guided catheter-based means that will provide arterial access to the brain.

While it had previously been demonstrated that a single intra-arterial administration of NRG1 prior to MCAO prevented neuronal death following ischemia and reperfusion, there was no indication that use at or after time of assault, whether mechanical (as with an infarct) or chemical, would be effective to ameliorate damage arising from the assault.

Neuregulin also has use, with similar dosage for intravenous administration in conjunction with reperfusion therapy such as anticoagulant therapy to ameliorate damage to the artery. In such instances, the neuregulin may be administered in carriers such as glucose, saline, Ringer's lactate, etc.

Agents with other mechanisms of action that prevent or avoid formation of obstructive occlusion such as those which cause clots to dissolve can also be used with neuregulin. In one embodiment, tissue plasminogen activator (t-PA) is used in conjunction with neuregulin. At present, use oft-PA remains limited and must be administered within three hours of the observed ischemic event. However, t-PA patients are at high risk of hemorrhagic transformation. Furthermore, t-PA causes inflammatory responses and reperfusion injury in the brain. The t-PA is administered intravenously in saline or similar carriers. In all instances, the neuregulin is most effective if administered into the carotid artery in a carrier containing serum albumin (in the case of humans, human serum albumin). The agents may be administered essentially simultaneously or the neuregulin may be administered within the 0-72 hour time period, though it is preferred practice to administer the neuregulin within 24 hours of administration of the t-PA.

While treatments cited above may be effective in limiting damage from a pathology-causing event, the recovery of function can take place only with regeneration of neuronal tissue. The administration of neuregulin into the ventricular-zone provides means for enhancing migration of stem cells which are formed in the ventricle to the site of neuronal damage.

Example 3

ErbB4 Receptors are Expressed Apoptotic and Degenerating Neurons

After erB4 immunohistochemistry, brain sections harvested from rats subjected to middle cerebral artery occlusion (MCAO) were stained with Fluoro-Jade, a marker for degenerating neurons, and with antibodies against ErbB4. As shown in FIGS. 4A-4F, many neurons in the cortex were Fluoro-Jade-positive (FIG. 4A). ErbB4 positive cells (FIG. 4B) were co-localized in Fluoro-Jade-positive neurons (FIG. 4C). Similarly, TUNEL staining (FIG. 4D) and ErbB4 (FIG. 4E) were double-labeled (FIG. 4F) in a subpopulation of cells in the ipsilateral brain.

Example 4

ErbB4 Expression is Upregulated in Macrophages/Microglia but not in Astrocytes Following MCAO Sections from the ipsilateral hemisphere of rats subjected to MCAO were double labeled with antibodies against erbB4 (FIG. 5A) and glial fibrillary acidic protein (GFAP) (FIG. 5B). Cells in the peri-infarct regions did not show co-localization of erbB4 and GFAP (FIG. 5C). Co-localization of erbB4 and Mac-1/CD11b indicated that ErbB4 is found in a subset of macrophages/microglia (FIG. 5D).

Example 5

NRG-1β Treatment Reduces MCAO/Reperfusion-Induced Brain Infarction

FIGS. 6A-6D show representative TTC stained brain sections from rats injected with vehicle (panel a; n=11), NRG1β (panel b; n=7) or NRG1α (panel c; n=3) before MCAO. NRG1β (2.5 µg/kg) or NRG1α (2.5 µg/kg) was given by a single intra-arterial injection immediately before MCAO. Adult male Sprague-Dawley rats weighing 250-300 g were used for this study. A total of 164 rats were used in this study. Rats were anesthetized with a ketamine/xylazine solution (10 mg/kg, IP) and subjected to left MCAO. MCAO was induced by the intraluminal suture method where the left common carotid artery (CCA) was exposed through a midline incision and was carefully dissected free from surrounding nerves and fascia. The occipital artery branches of the external carotid artery (ECA) were then isolated, and the occipital artery and superior thyroid artery branches of the ECA were coagulated. The ECA was dissected further distally. The internal carotid artery (ICA) was isolated and carefully separated from the adjacent vagus nerve, and the pterygopalatine artery was ligated close to its origin with a 6-0 silk suture. Then, a 40 mm 3-0 surgical monofilament nylon suture (Harvard Apparatus, Holliston, Mass.) was coated with poly-L-lysine with its tip rounded by heating near a flame. The filament was inserted from the ECA into the ICA and then into the circle of Willis to occlude the origin of the left MCA. The suture was inserted 18 to 20 mm from the bifurcation of the CCA to occlude the MCA. After 1.5 hour of ischemia, the nylon suture was withdrawn and the ischemic brain tissue was reperfused for 24 hours before sacrificing. Core body temperature was monitored with a rectal probe and maintained at 37° C. with a Homeothermic Blanket Control Unit (Harvard Apparatus) during anesthesia. To determine the effects of NRG-1 on ischemic stroke, rat were injected intravascularly with a single bolus 10 µl dose of vehicle (1% BSA in PBS) or NRG-1β (1-50 umol/L NRG-1 (EGF-like domain, R&D Systems, Minneapolis, Minn.) dissolved in 1% BSA/PBS) through a Hamilton syringe at a rate of 5 µl/min. This resulted in the administration of 0.5-2.5 µg of NRG-1/kg body weight. NRG-1 or vehicle was administered by bolus injection into the ICA through ECA. Solutions were administered either before MCAO or immediately following 1.5 hours of MCAO and either 0, 4 or 12 hours of reperfusion. Animals were sacrificed 24 hours after reperfusion or after 14 days for the long-term studies. Animals were killed 24 hours later and the brains were sliced into 2 mm sections and stained with 2,3, 5-triphenyltetrazolium chloride (TTC). Infarct volumes in brains from vehicle and NRG1 treated animals are shown in the graph (FIG. 6D). The data demonstrate that NRG1β treatment reduces MCAO/reperfusion-induced brain infarction.

Example 6

NRG-1β Suppresses MCAO/Reperfusion-Induced Apoptotic Damage in Rat Brain

Figure 7A:
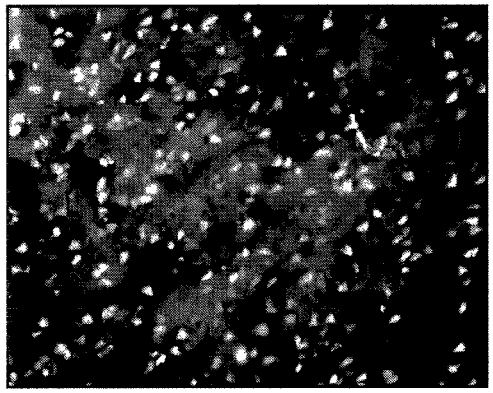
FIGS. 7A-7E are pictures showing that NRG1β suppresses MCAO/reperfusion-induced apoptotic damage in rat brain. Rats were subjected to MCAO for 1.5 hours followed by reperfusion for 24 hours (representative views are shown for TUNEL labeling of rat brain sections; n=5 for each condition). TUNEL staining is found in the cortex (FIG. 7A) and striatum (FIG. 7B) following MCAO while no TUNEL staining is seen in the cortex (FIG. 7C) and reduced levels are seen in the striatum (FIG. 7D) in NRG1β-treated rats. The coronal brain image (~bregma+1.2 mm) indicates the areas observed in the sections (FIG. 7E). Scale bar is 100 uM.
Figure 7B:
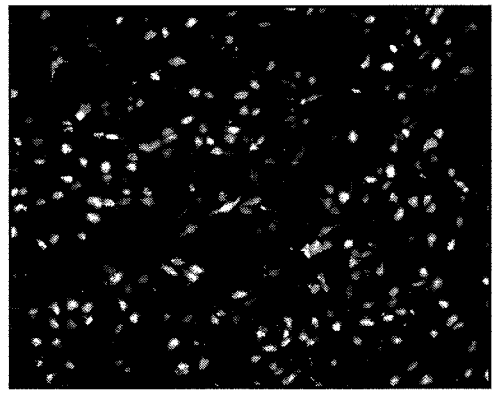
Figure 7C:
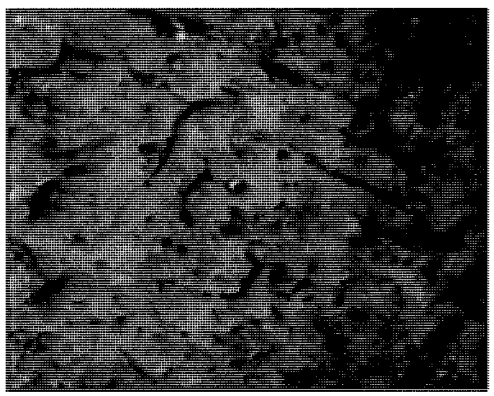
Figure 7D:
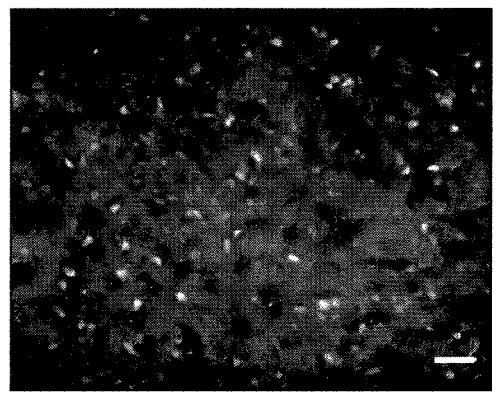
Figure 7E:
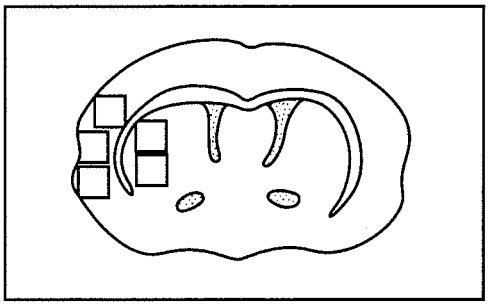

Rats were subjected to MCAO for 1.5 hours followed by reperfusion for 24 hours. FIGS. 7A-7E show representative views of TUNEL labeling of rat brain sections (n=5 for each condition). TUNEL assay was performed with a DeadEND Fluorometric TUNEL System (Promega, Madison, Wis.) according to the manufacturer's instructions. Slides were then washed with PBS and mounted with Vectashield Mounting Medium containing DAPI. All sections were examined by fluorescence microscopy in three random middle cerebral artery served areas in the inner border of the infarct in the ischemic front-parietal cortex of each rat. In animals given vehicle or neuregulin-1, cortex and striatum were examined in three or more 20 µm sections per animal. TUNEL staining was found in the cortex (FIG. 7A) and striatum (FIG. 7B) following MCAO while no TUNEL staining was seen in the cortex (FIG. 7C) and reduced levels were seen in the striatum (FIG. 7D) in NRG1β-treated rats. The coronal brain image (~bregma+1.2 mm) indicates the areas observed in the sections (FIG. 7E).

Example 7

NRG-1 Treatment Reduces MCAO/Reperfusion-Induced Brain Infarction

Figure 8A:
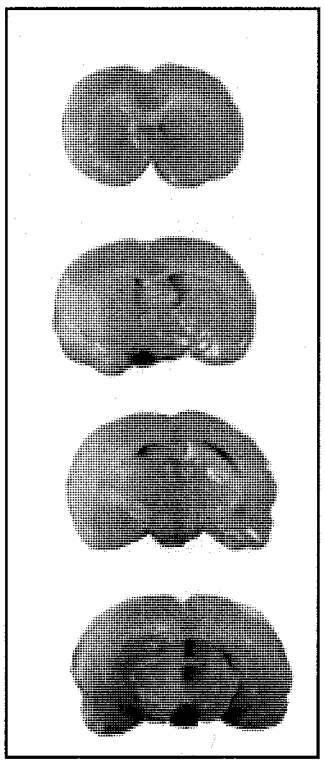
FIGS. 8A-8E are pictures and graphs showing that NRG1 treatment reduces MCAO/reperfusion-induced brain infarction. Representative TTC stained coronal brain sections are shown where rats were injected with vehicle (FIG. 8A) or NRG1 immediately after MCAO (FIG. 8B) and 4 hours after reperfusion (FIG. 8C). Infarct volumes in brains from rats treated with vehicle (n=10) or NRG1 immediately after MCAO (R0; n=8), 4 hours after reperfusion (R4; n=6) or 12 hours after reperfusion (R12; n=8) are show in the graph (FIG. 8D). Values are presented as mean±SD of all infarct volumes for each experimental condition; * denotes significantly different from respective vehicle treated animals (P<0.01). The time line (FIG. 8E) illustrates the MCAO protocol and NRG1 injections.
Figure 8B:
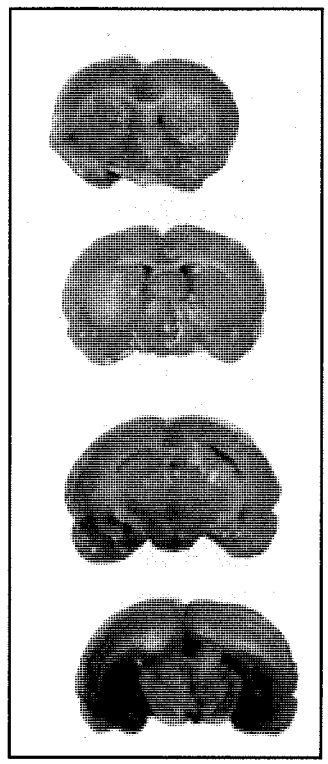
Figure 8C:
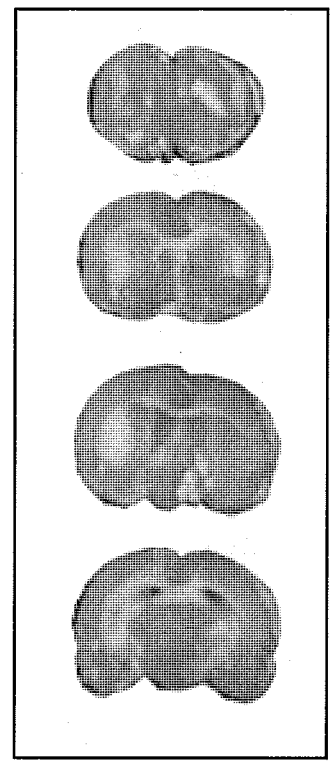
Figure 8D:
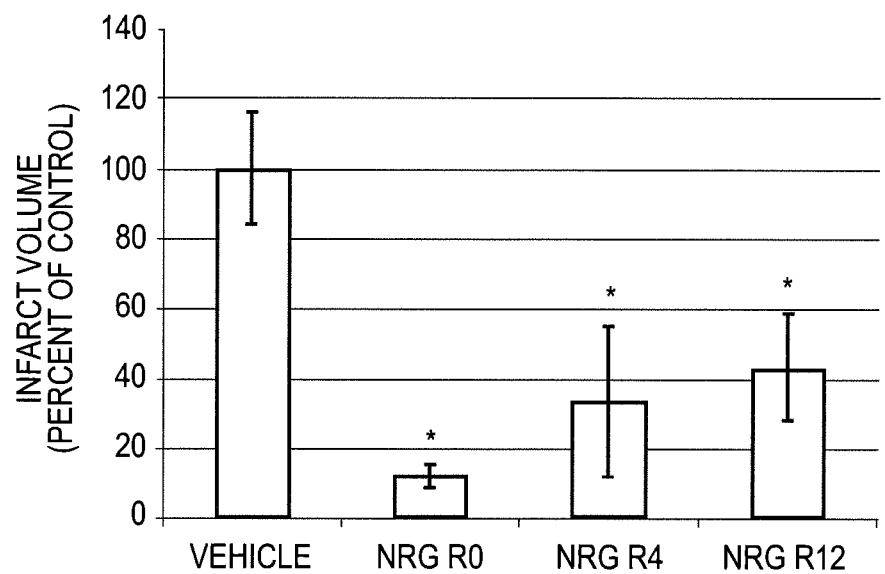
Figure 8E:
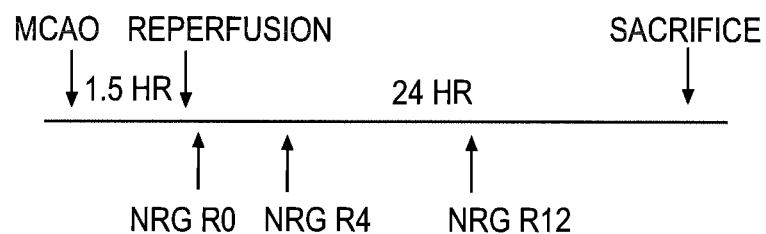

FIGS. 8A-8E show] representative TTC stained coronal brain sections from rats injected with vehicle (FIG. 8A) or NRG1 immediately after MCAO (FIG. 8B) and 4 hours after reperfusion (FIG. 8C). Infarct volumes in brains from rats treated with vehicle (n=10) or NRG1 immediately after MCAO (R0; n=8), 4 hours after reperfusion (R4; n=6) or 12 hours after reperfusion (R12; n=8) are show in the graph (FIG. 8D). The time line (FIG. 8E) illustrates the MCAO protocol and NRG1 injections.

Example 8

Figure 9:
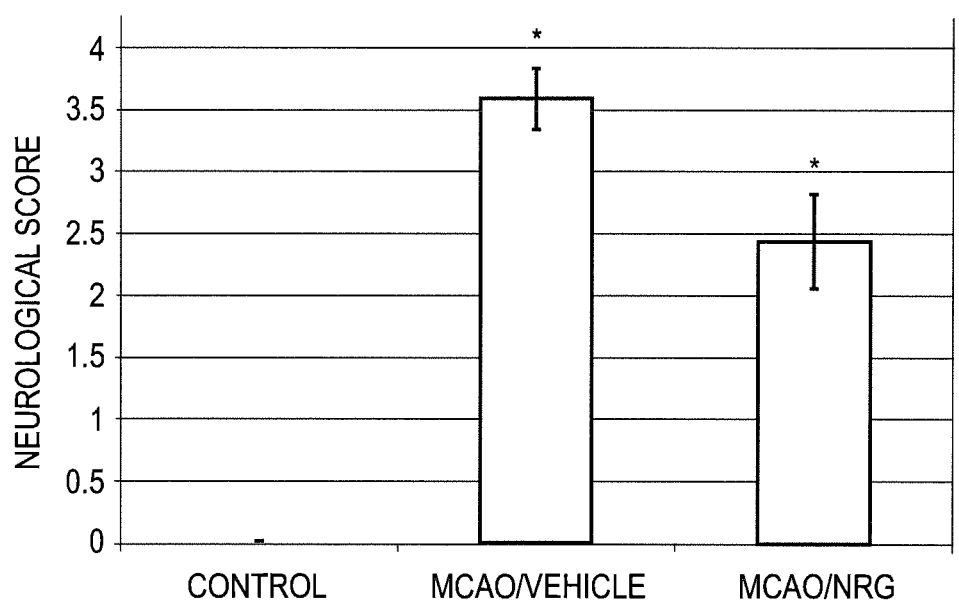
FIG. 9 is a graph showing that NRG1 administration resulted in a significant improvement in neurological outcome (* denotes P<0.01). NRG1 was administered after MCAO and 4 hours of reperfusion. Neurological function was graded on a scale of 0-4 (normal score 0, maximal deficit score 4). All animals were tested prior to surgery (controls; n=14) and after treatment with NRG1 or vehicle. The NRG1 treated group (n=9) displayed a 33% improvement in neurological score compared with vehicle treated rats (n=5).

NRG-1 Administration Resulted in a Significant Improvement in Neurological Outcome NRG1 was administered after MCAO and 4 hours of reperfusion. As shown in FIG. 9, neurological function was graded on a scale of 0-4 (normal score 0, maximal deficit score 4). All animals were tested prior to surgery (controls; n=14) and after treatment with NRG-1 or vehicle. The NRG1 treated group (n=9) displayed a 33% improvement in neurological score compared with vehicle treated rats (n=5).

Example 9

NRG1β Prevents Microglial and Astrocytic Activation Following MCAO

Figure 10A:
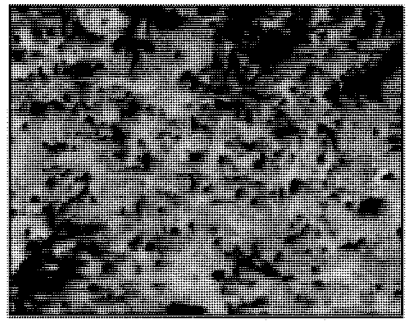
FIGS. 10A-10F are pictures showing that NRG1β prevents microglial and astrocytic activation following MCAO. Rats were subjected to MCAO followed by reperfusion for 24 hours (n=5 for each condition). NRG1β or vehicle was injected into the ECA. Sections were labeled for immunohistochemistry with an antibody against ED-1. While no staining was seen in the contralateral side (FIG. 10A), ED-1 labeled cells are present in the ipsilateral hemisphere (FIG. 10B) following MCAO in vehicle-treated animals. Few ED-1 positive cells are found in animals treated with NRG-1β (FIG. 10C). Examples of ED-1 positive cells are indicated by the arrows. Scale bar is 50 μM. To assess astrocytic activation, sections were labeled for immunohistochemistry with an antibody against GFAP. Compared to the contralateral control (FIG. 10D), heavy GFAP staining is found at the border or infarct (FIG. 10E) following MCAO in vehicle-treated animals. However, when rats were treated with NRG1β, GFAP expression was dramatically reduced in the peri-infarct regions (FIG. 10F). * denotes infarct core or the corresponding region in the contralateral control; # denotes non-ischemic tissues or the corresponding region in the contralateral control. Scale bar is 100 μM.
Figure 10D:
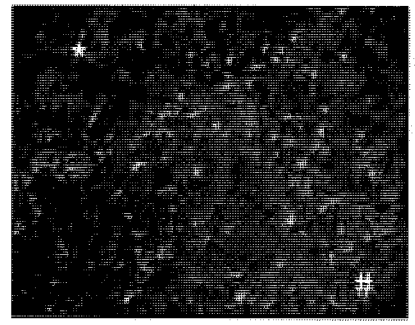
Figure 10B:
Figure 10E:
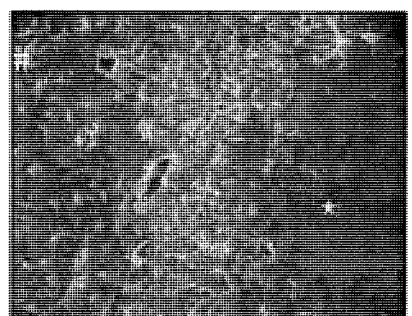
Figure 10C:
Figure 10F:
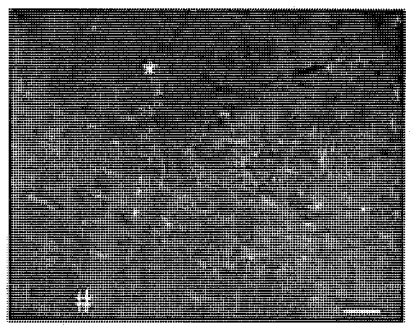

Rats were subjected to MCAO followed by reperfusion for 24 hours (n=5 for each condition). NRG1β or vehicle was injected intraarterially as described above. Sections were labeled for immunohistochemistry with an antibody against ED-1. As shown in FIGS. 10A-10F, while no staining was seen in the contralateral side (FIG. 10A), ED-1 labeled cells are present in the ipsilateral hemisphere (FIG. 10B) following MCAO in vehicle-treated animals. Few ED-1 positive cells are found in animals treated with NRG1β (FIG. 10C). To assess astrocytic activation, sections were labeled for immunohistochemistry with an antibody against GFAP. Compared to the contralateral control (FIG. 10D), heavy GFAP staining is found at the border or infarct (FIG. 10E) following MCAO in vehicle-treated animals. However, when rats were treated with NRG-1β, GFAP expression was dramatically reduced in the peri-infarct regions (FIG. 10F).

Example 10

NRG1β Reduces MCAO/Reperfusion-Induced IL-1β mRNA Levels

Figure 11:
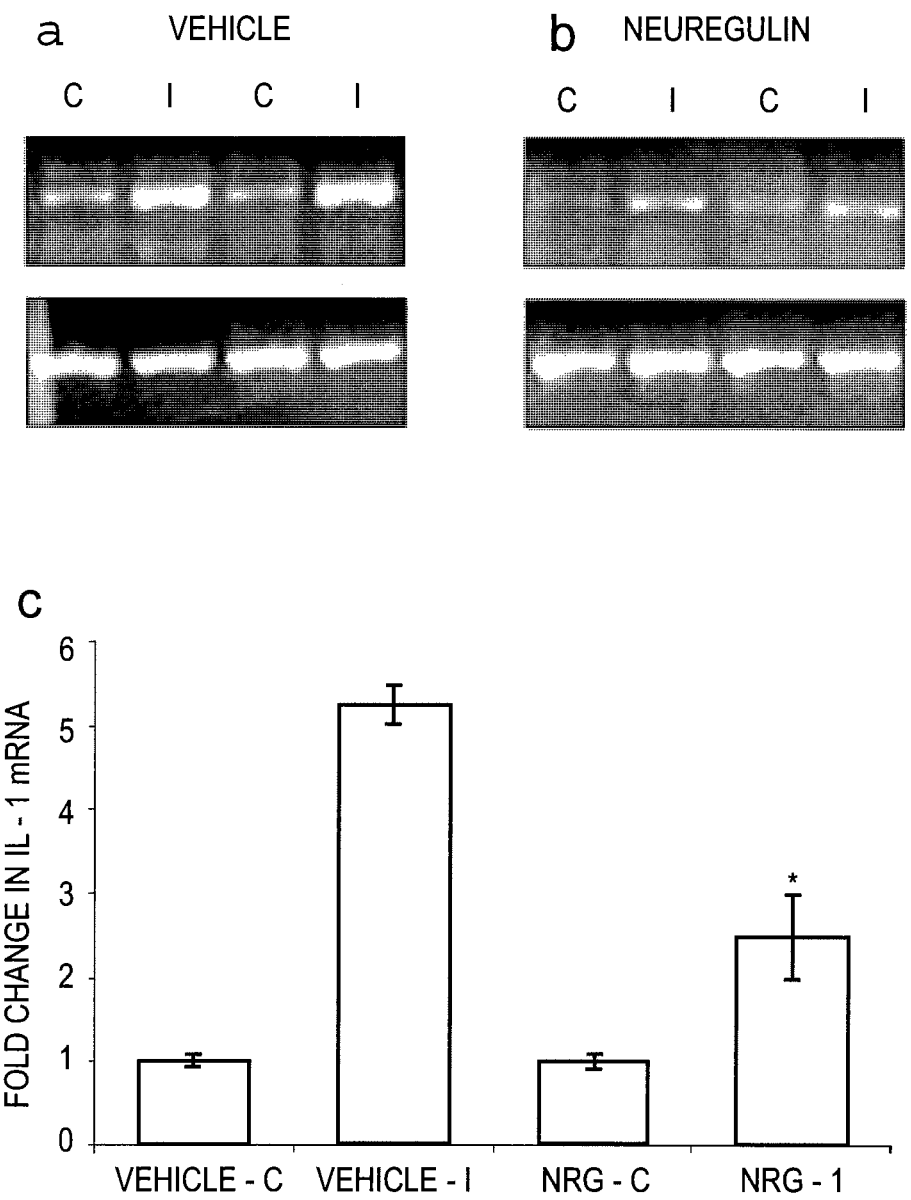
FIG. 11 is a composite of pictures and graphs showing that NRG1β reduces MCAO/reperfusion-induced IL-1β mRNA levels. Rats were treated with NRG1β or vehicle then subjected to MCAO. RNA was isolated and IL-1β mRNA expression was measured by RT-PCR. The expression of IL-1 (panel a) and GAPDH (panel b) mRNA is shown (n=4 for each condition). Panel c shows the average percentage of change±SEM in IL-1 mRNA levels from NRG-β-treated rat compared to vehicle-treated controls after normalization to GAPDH (* denotes P<0.05). I=ipsilateral hemisphere; C=contralateral hemisphere.

Rats were treated with NRG1β or vehicle then subjected to MCAO. RNA was isolated and IL1β mRNA expression was measured by RT-PCR. FIG. 11 shows the mRNA expression levels of IL-1 (panel a) and GAPDH (panel b) (n=4 for each condition). Panel c shows the average percentage of change±SEM in IL-1 mRNA levels from NRG1β-treated rat compared to vehicle-treated controls after normalization to GAPDH.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

The invention claimed is:

1. A method for ameliorating neuronal damage in a subject, comprising: administering to said subject an effective amount of a pharmaceutical composition comprising: a chimeric neuregulin polypeptide having an integrin domain that binds to an integrin and an ErbB3/B4 binding domain that binds to ErbB3 and/or ErbB4, said chimeric neuregulin polypeptide comprising: a neuregulin backbone derived from a native neuregulin polypeptide, said neuregulin backbone comprising an ErbB3/B4 binding domain; and a donor fragment comprising a polypeptide derived from another neuregulin that is different from said native neuregulin, said donor fragment comprising an integrin binding domain, wherein said chimeric neuregulin comprises a neuregulin consensus motif comprising six cysteine residues spread in a region spanning an integrin binding domain and an ErbB3/ErbB4 binding domain and wherein said integrin binding domain comprises two positively charged amino acids at the amino-end of the first cysteine in the neuregulin consensus sequence, wherein the chimeric neuregulin polypeptide comprises the amino acid sequence selected from the group consisting of SEQ ID NOs: 22, 23, 24, 27 and 28, and a pharmaceutically acceptable carrier.

2. The method of claim 1, wherein said neuronal damage is caused by an occlusive stroke and wherein said pharmaceutical composition is administered within 72 hours of said occlusive stroke.

3. The method of claim 2, wherein said pharmaceutical composition is administered in conjunction with t-PA.

4. The method of claim 2, wherein said pharmaceutical composition is administered in conjunction with a glutamate receptor inhibitor.

5. The method of claim 2, wherein said pharmaceutical composition is administered after the initial inflammation due to the occlusive stroke has subsided to enhance migration of stem cells from a ventricle into an area of the brain damaged by the occlusive stroke.

6. The method of claim 1, wherein said neuronal damage is caused by exposure to a neurotoxin and wherein said pharmaceutical composition is administered within 72 hours of said exposure.

7. The method of claim 6, wherein said neurotoxin is an organophosphate.

8. The method of claim 6, wherein the composition is administered in conjunction with an antidote to neurotoxin or an anticonvulsant.

9. The method of claim 1, wherein said neuronal damage is caused by acute CNS injuries, and wherein said composition is administered within 72 hours of the cause of CNS injury.

10. The method of claim 1, wherein said neuronal damage is caused by a neurodegenerative disorder.

11. The method of claim 10, wherein said neurodegenerative disorder is Alzheimer's disease, Parkinson's disease, Huntington's disease or amyotrophic lateral sclerosis.

12. A method for ameliorating secondary neuronal injury and inflammation following traumatic brain injury (TBI) in a subject, comprising: administering to said subject an effective amount of a pharmaceutical composition comprising: a chimeric neuregulin polypeptide having an integrin domain that binds to an integrin and an ErbB3/B4 binding domain that binds to ErbB3 and/or ErbB4, said chimeric neuregulin polypeptide comprising: a neuregulin backbone derived from a native neuregulin polypeptide, said neuregulin backbone comprising an ErbB3/B4 binding domain; and a donor fragment comprising a polypeptide derived from another neuregulin that is different from said native neuregulin, said donor fragment comprising an integrin binding domain, wherein said chimeric neuregulin comprises a neuregulin consensus motif comprising six cysteine residues spread in a region spanning an integrin binding domain and an ErbB3/ErbB4 binding domain and wherein said integrin binding domain comprises two positively charged amino acids at the amino-end of the first cysteine in the neuregulin consensus sequence, wherein the chimeric neuregulin polypeptide comprises the amino acid sequence selected from the group consisting of SEQ ID NOs: 22, 23, 24, 27 and 28, and a pharmaceutically acceptable carrier.

13. A method for ameliorating blood vessel damage caused by acute mechanical or chemical assault in a subject, comprising: administering to said subject an effective amount of a pharmaceutical composition comprising: a chimeric neuregulin polypeptide having an integrin domain that binds to an integrin and an ErbB3/B4 binding domain that binds to ErbB3 and/or ErbB4, said chimeric neuregulin polypeptide comprising: a neuregulin backbone derived from a native neuregulin polypeptide, said neuregulin backbone comprising an ErbB3/B4 binding domain; and a donor fragment comprising a polypeptide derived from another neuregulin that is different from said native neuregulin, said donor fragment comprising an integrin binding domain, wherein said chimeric neuregulin comprises a neuregulin consensus motif comprising six cysteine residues spread in a region spanning an integrin binding domain and an ErbB3/ErbB4 binding domain and wherein said integrin binding domain comprises two positively charged amino acids at the amino-end of the first cysteine in the neuregulin consensus sequence, wherein the chimeric neuregulin polypeptide comprises the amino acid sequence selected from the group consisting of SEQ ID NOs: 22, 23, 24, 27 and 28, and a pharmaceutically acceptable carrier.

14. The method of claim 13, wherein said blood vessel damage is caused by placement of a balloon or stent in a blood vessel, diagnostic cardiac catheterization, or cardiac surgery.

\* \* \* \* \*